US009931025B1

(12) United States Patent
Graetzel et al.

(10) Patent No.: US 9,931,025 B1
(45) Date of Patent: Apr. 3, 2018

(54) AUTOMATED CALIBRATION OF ENDOSCOPES WITH PULL WIRES

(71) Applicant: Auris Surgical Robotics, Inc., San Carlos, CA (US)

(72) Inventors: Chauncey F. Graetzel, Palo Alto, CA (US); Ritwik Ummalaneni, San Mateo, CA (US)

(73) Assignee: Auris Surgical Robotics, Inc., Redwood City, CA (US)

( * ) Notice: Subject to any disclaimer, the term of this patent is extended or adjusted under 35 U.S.C. 154(b) by 0 days.

(21) Appl. No.: 15/282,079

(22) Filed: Sep. 30, 2016

(51) Int. Cl.
| | |
|---|---|
| *A61B 1/01* | (2006.01) |
| *A61B 1/00* | (2006.01) |
| *A61B 1/005* | (2006.01) |
| *A61B 1/018* | (2006.01) |
| *A61B 90/00* | (2016.01) |
| *G01B 21/16* | (2006.01) |

(52) U.S. Cl.
CPC ............ *A61B 1/01* (2013.01); *A61B 1/00006* (2013.01); *A61B 1/0051* (2013.01); *A61B 1/00149* (2013.01); *A61B 1/018* (2013.01); *A61B 90/06* (2016.02); *G01B 21/16* (2013.01); *A61B 1/00057* (2013.01)

(58) Field of Classification Search
CPC ....... A61B 1/01; A61B 90/06; A61B 1/00006; A61B 1/00149; A61B 1/0051; A61B 1/018; G01B 21/16
See application file for complete search history.

(56) References Cited

U.S. PATENT DOCUMENTS

| | | | | |
|---|---|---|---|---|
| 5,408,263 A | * | 4/1995 | Kikuchi | ............. A61B 1/00059 348/223.1 |
| 9,622,827 B2 | | 4/2017 | Yu | |
| 9,727,963 B2 | | 8/2017 | Mintz | |
| 9,763,741 B2 | * | 9/2017 | Alvarez | ................. A61B 34/30 |
| 9,788,910 B2 | * | 10/2017 | Schuh | ..................... A61B 34/30 |
| 2003/0045778 A1 | * | 3/2003 | Ohline | ................. A61B 1/0053 600/114 |
| 2005/0065400 A1 | * | 3/2005 | Banik | ................ A61B 1/00059 600/109 |
| 2005/0261551 A1 | | 11/2005 | Couvillon | |
| 2007/0150155 A1 | * | 6/2007 | Kawai | ................ A61B 1/00059 701/72 |

(Continued)

*Primary Examiner* — Lisa Caputo
*Assistant Examiner* — Philip Cotey
(74) *Attorney, Agent, or Firm* — Knobbe Martens Olson & Bear LLP

(57) ABSTRACT

A surgical robotic system automatically calibrates tubular and flexible surgical tools such as endoscopes. By compensating for unideal behavior of an endoscope, the surgical robotic system can accurately model motions of the endoscope and navigate the endoscope while performing a surgical procedure on a patient. During calibration, the surgical robotic system moves the endoscope to a target position and receives data describing an actual position and/or orientation of the endoscope. The surgical robotic system determines gain values based at least on the discrepancy between the target position and the actual position. The endoscope can include tubular components referred to as a sheath and leader. An instrument device manipulator of the surgical robotic system actuates pull wires coupled to the sheath and/or the leader, which causes the endoscope to articulate.

32 Claims, 25 Drawing Sheets

(56) References Cited

U.S. PATENT DOCUMENTS

| | | | |
|---|---|---|---|
| 2007/0287992 A1* | 12/2007 | Diolaiti | G05B 19/19 606/1 |
| 2008/0255505 A1* | 10/2008 | Carlson | A61B 19/2203 604/95.04 |
| 2009/0076534 A1* | 3/2009 | Shelton, IV | A61B 17/07207 606/170 |
| 2009/0245600 A1* | 10/2009 | Hoffman | A61B 1/00039 382/128 |
| 2010/0076263 A1 | 3/2010 | Tanaka | |
| 2011/0137122 A1* | 6/2011 | Kawai | A61B 1/0052 600/118 |
| 2012/0046522 A1* | 2/2012 | Naito | A61B 1/00006 600/118 |
| 2012/0123441 A1* | 5/2012 | Au | A61B 19/2203 606/130 |
| 2012/0209293 A1* | 8/2012 | Carlson | A61B 19/2203 606/130 |
| 2012/0253276 A1* | 10/2012 | Govari | A61M 25/0147 604/95.01 |
| 2013/0090530 A1 | 4/2013 | Ramamurthy | |
| 2013/0102846 A1* | 4/2013 | Sjostrom | A61B 1/07 600/110 |
| 2014/0163664 A1* | 6/2014 | Goldsmith | A61B 17/00491 623/1.11 |
| 2015/0088161 A1* | 3/2015 | Hata | A61B 19/2203 606/130 |
| 2015/0119637 A1* | 4/2015 | Alvarez | A61B 1/0057 600/102 |
| 2015/0119638 A1 | 4/2015 | Yu | |
| 2015/0164594 A1 | 6/2015 | Romo | |
| 2015/0164595 A1 | 6/2015 | Bogusky | |
| 2015/0164596 A1 | 6/2015 | Romo | |
| 2015/0202015 A1* | 7/2015 | Elhawary | A61B 19/2203 606/130 |
| 2016/0001038 A1 | 1/2016 | Romo | |
| 2016/0016319 A1* | 1/2016 | Remirez | B25J 18/06 74/490.04 |
| 2016/0184032 A1 | 6/2016 | Romo | |
| 2016/0270866 A1 | 9/2016 | Yu | |
| 2016/0287840 A1 | 10/2016 | Jiang | |
| 2016/0338787 A1 | 11/2016 | Popovic | |
| 2016/0346924 A1* | 12/2016 | Hasegawa | B25J 9/1612 |
| 2016/0360949 A1* | 12/2016 | Hyodo | B25J 9/1045 |
| 2016/0374541 A1 | 12/2016 | Agrawal | |
| 2017/0065357 A1 | 3/2017 | Schuh | |
| 2017/0065363 A1 | 3/2017 | Schuh | |
| 2017/0065364 A1 | 3/2017 | Schuh | |
| 2017/0065365 A1 | 3/2017 | Schuh | |
| 2017/0100199 A1 | 4/2017 | Yu | |
| 2017/0119411 A1 | 5/2017 | Shah | |
| 2017/0119412 A1 | 5/2017 | Noonan | |
| 2017/0119413 A1 | 5/2017 | Romo | |
| 2017/0119481 A1 | 5/2017 | Romo | |

* cited by examiner

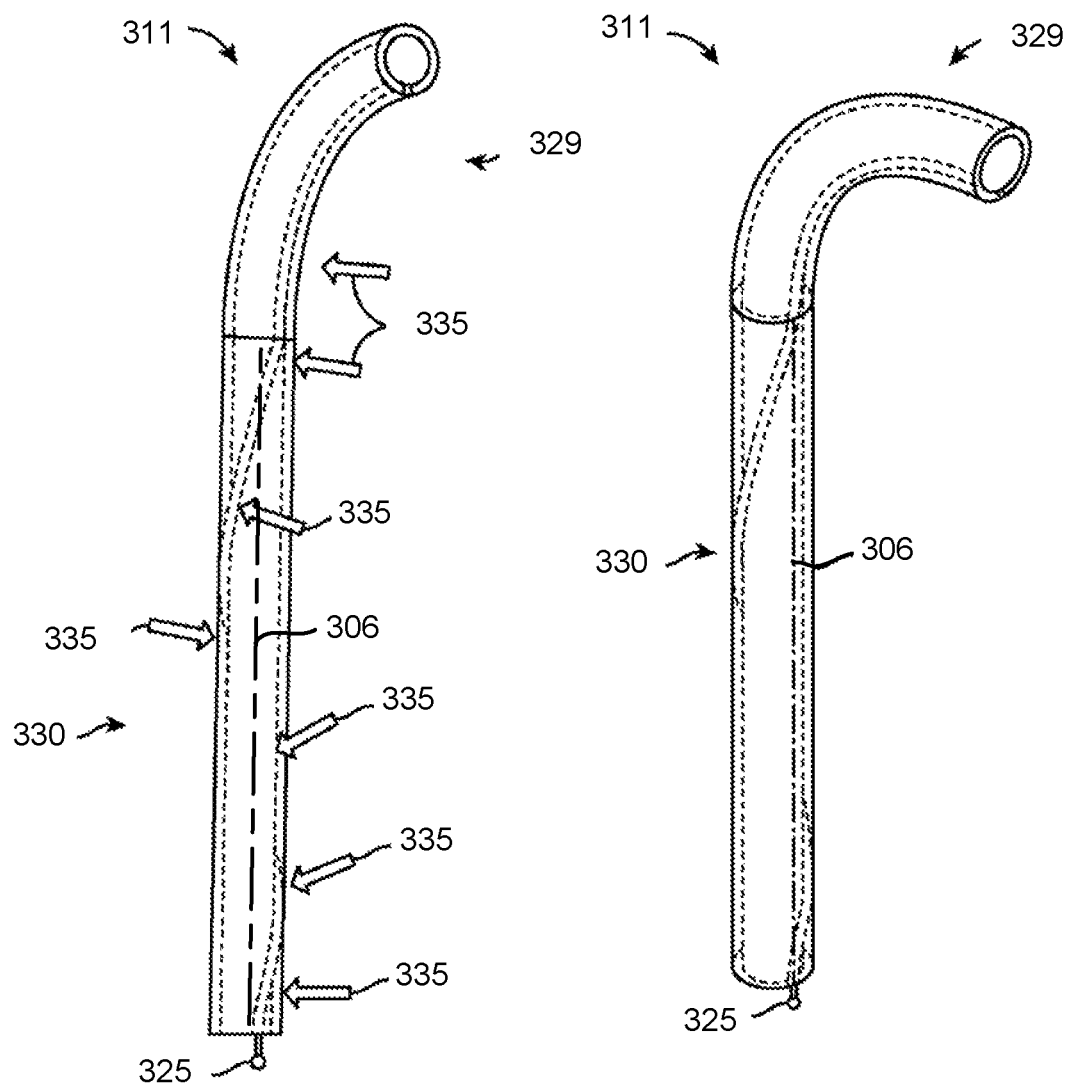
FIG. 3F  FIG. 3G

Resting Position

Articulate to Target Deflection of
90 Degrees in Positive Pitch Direction
Unideal Offset in Positive Pitch Direction Articulate to Target Deflection of
90 Degrees in Positive Pitch Direction Additional Unideal Offset in Positive Yaw Direction Resting Position Articulate to Target Deflection of 90 Degrees in Positive Pitch Direction Unideal Offset in Roll Direction

900

Retrieve default gain values for an endoscope including pull wires, a leader, and a sheath.
910

Insert the endoscope into a patient.
920

Receive information about a roll angle of the leader relative to the sheath and a length of the leader enclosed by the sheath.
930

Provide a command to move the endoscope.
940

Receive spatial data of the endoscope.
950

Determine a new gain value.
960

Store the new gain value.
970

FIG. 9

AUTOMATED CALIBRATION OF ENDOSCOPES WITH PULL WIRES

CROSS-REFERENCE TO RELATED APPLICATIONS

The subject matter of the present application is related to U.S. application Ser. No. 14/523,760, filed on Oct. 24, 2014, entitled "SYSTEM FOR ROBOTIC-ASSISTED ENDOLUMENAL SURGERY AND RELATED METHODS", the entire disclosure of which is incorporated herein by reference.

BACKGROUND

1. Field of Art

This description generally relates to surgical robotics, and particularly to an automated process for calibrating endoscopes with pull wires.

2. Description of the Related Art

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians have started using robotic arms to help perform surgical procedures. For instance, physicians use robotic arms to control surgical instruments such as endoscopes.

Endoscopes with movable tips help perform surgical procedures in a minimally invasive manner. A movable tip can be directed to a remote location of a patient, such as the lung or blood vessel. Deviation of the tip's actual position from a target position may result in additional manipulation to correct the tip's position. Existing techniques for manual calibration may rely on limited amounts of endoscope tip deflection that does not accurately model motions of the tip.

SUMMARY

A surgical robotic system automatically calibrates tubular and flexible surgical tools such as endoscopes. By compensating for unideal behavior of an endoscope, the surgical robotic system can accurately model motions of the endoscope and navigate the endoscope while performing a surgical procedure on a patient. During calibration, the surgical robotic system moves the endoscope to a target position and receives calibration data describing an actual position of the endoscope. The surgical robotic system determines the actual position and/or orientation that the endoscope moves in response to commands based on calibration data captured by spatial sensors. Example spatial sensors include accelerometers, gyroscopes, electromagnetic sensors, optical fibers, cameras, and fluoroscopic imaging systems. The surgical robotic system determines gain values based at least on the discrepancy between the target position and the actual position. The surgical robotic system can perform calibration before or during a surgical procedure.

In some embodiments, an endoscope includes tubular components referred to as a sheath and leader. The gain values may also be based on a length of the leader extending out of the sheath, or a relative roll angle of the leader relative to the sheath. The surgical robotic system moves the sheath and leader using an instrument device manipulator (IDM). For example, the IDM translates pull wires coupled to the sheath or the leader, which causes the endoscope to move along different axis, e.g., a pitch, yaw, and roll axis.

BRIEF DESCRIPTION OF DRAWINGS

FIG. 3F is a side view of a sheath of an endoscope with a helix section according to one embodiment.

FIG. 3G is another view of the sheath of the endoscope shown in FIG. 3F according to one embodiment.

FIG. 9 is a flowchart of a process for intraoperative automated calibration of an endoscope to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

The methods and apparatus disclosed herein are well suited for use with one or more endoscope components or steps as described in U.S. application Ser. No. 14/523,760, filed on Oct. 24, 2014, published as U.S. Pat. Pub. No. US 2015/0119637, entitled "SYSTEM FOR ROBOTIC-ASSISTED ENDOLUMENAL SURGERY AND RELATED METHODS," the full disclosure of which has been previously incorporated by reference. The aforementioned application describes system components, endolumenal systems, virtual rail configurations, mechanism changer interfaces, instrument device manipulators (IDMs), endoscope tool designs, control consoles, endoscopes, instrument device manipulators, endolumenal navigation, and endolumenal procedures suitable for combination in accordance with embodiments disclosed herein.

I. Surgical Robotic System

Figure 1:
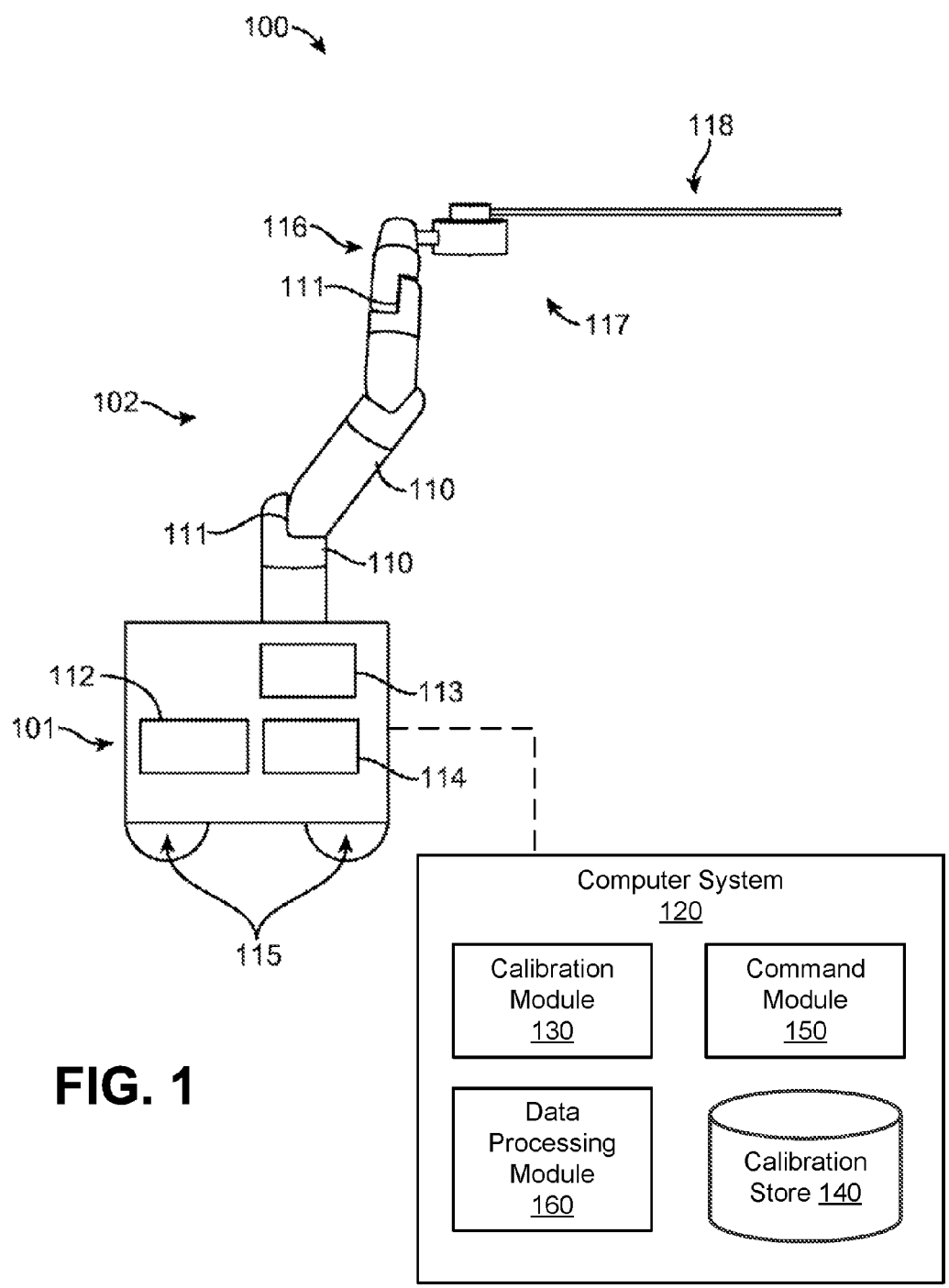
FIG. 1 illustrates a surgical robotic system according to one embodiment.

FIG. 1 illustrates a surgical robotic system 100 according to one embodiment. The surgical robotic system 100 includes a base 101 coupled to one or more robotic arms, e.g., robotic arm 102. The base 101 is communicatively coupled to a command console, which is further described with reference to FIG. 2 in Section II. Command Console. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-I in Section III. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit unideal behavior in response to forces applied by the elongate movement members. The unideal behavior may be due to imperfections or variations in stiffness and compressibility of the endoscope 118, as well as variability in slack or stiffness between different elongate movement members.

The surgical robotic system 100 includes a computer system 120, for example, a computer processor. The computer system 120 includes a calibration module 130, calibration store 140, command module 150, and data processing module 160. The data processing module 160 can process calibration data collected by the surgical robotic system 100. The calibration module 130 can characterize the unideal behavior of the endoscope 118 using gain values based on the calibration data. The computer system 120 and its modules are further described in Section VII: Calibration Process Flows. The surgical robotic system 100 can more accurately control an endoscope 118 by determining accurate values of the gain values. In some embodiments, some or all functionality of the computer system 120 is performed outside the surgical robotic system 100, for example, on another computer system or server communicatively coupled to the surgical robotic system 100.

II. Command Console

Figure 2:
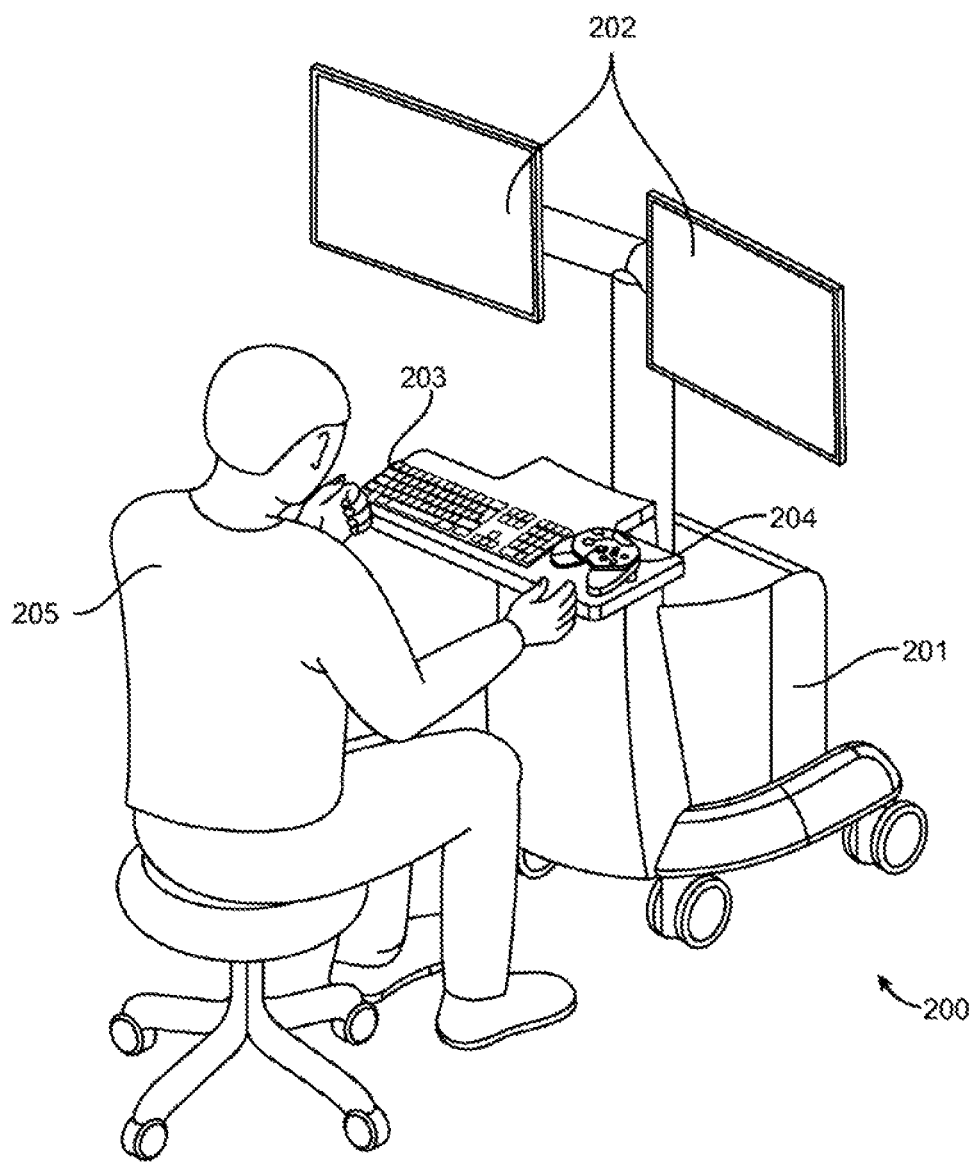
FIG. 2 illustrates a command console for a surgical robotic system according to one embodiment.

FIG. 2 illustrates a command console 200 for a surgical robotic system 100 according to one embodiment. The command console 200 includes a console base 201, display modules 202, e.g., monitors, and control modules, e.g., a keyboard 203 and joystick 204. In some embodiments, one or more of the command module 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay pre-determined optimal navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Endoscope

Figure 3A:
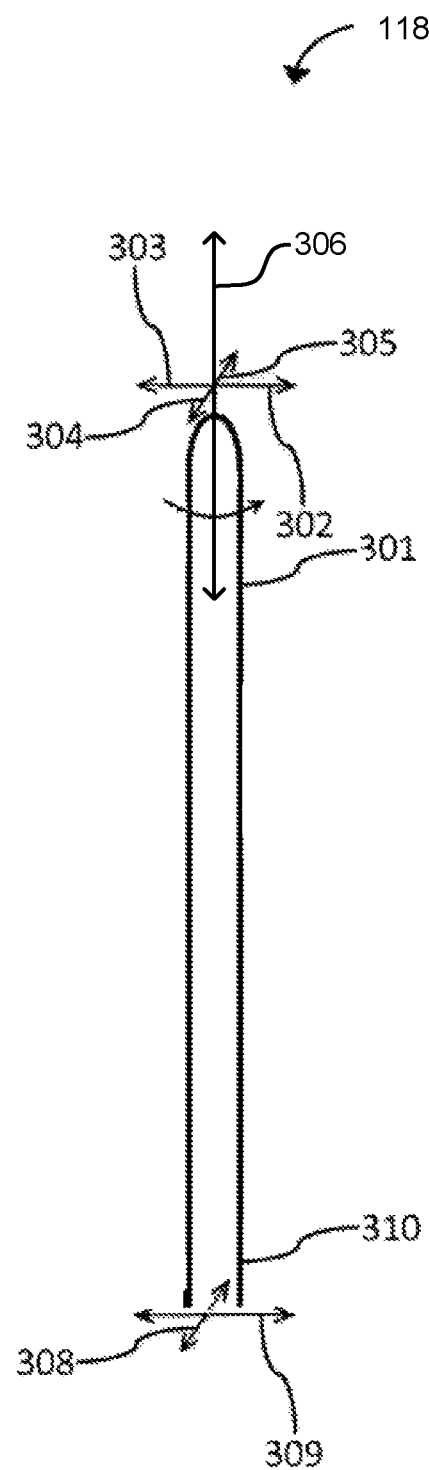
FIG. 3A illustrates multiple degrees of motion of an endoscope according to one embodiment.

FIG. 3A illustrates multiple degrees of motion of an endoscope 118 according to one embodiment. The endoscope 118 is an embodiment of the endoscope 118 shown in FIG. 1. As shown in FIG. 3A, the tip 301 of the endoscope 118 is oriented with zero deflection relative to a longitudinal axis 306 (also referred to as a roll axis 306). To capture images at different orientations of the tip 301, a surgical robotic system 100 deflects the tip 301 on a positive yaw axis 302, negative yaw axis 303, positive pitch axis 304, negative pitch axis 305, or roll axis 306. The tip 301 or body 310 of the endoscope 118 may be elongated or translated in the longitudinal axis 306, x-axis 308, or y-axis 309.

Figure 3B:
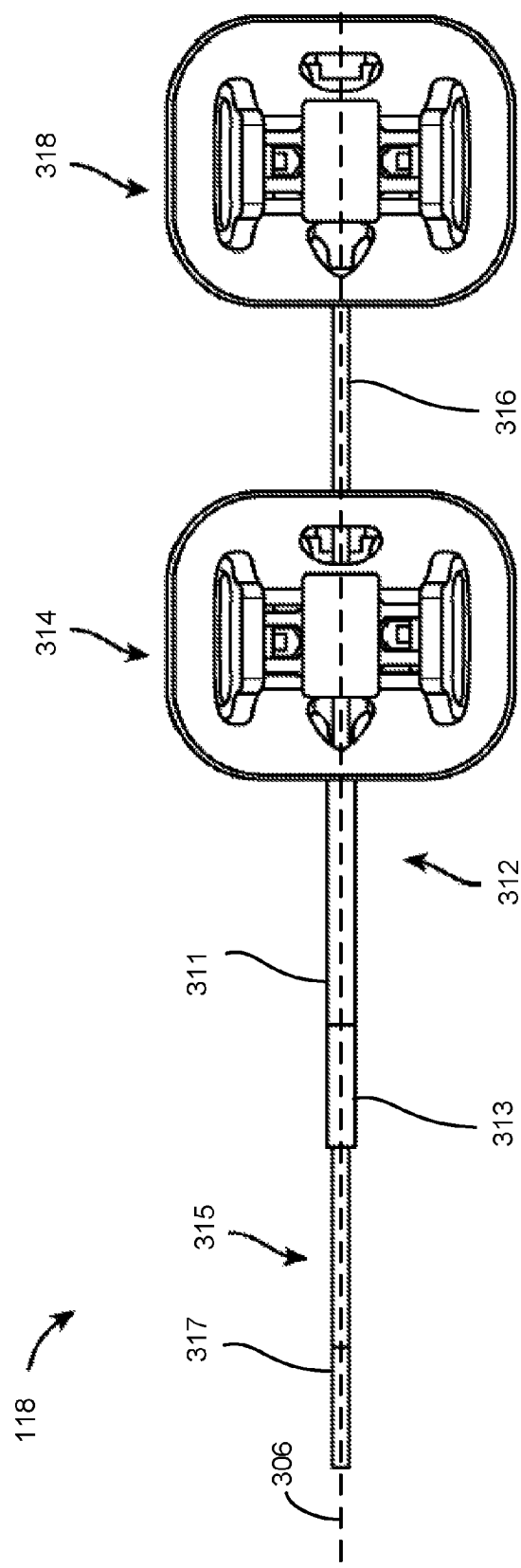
FIG. 3B is a top view of an endoscope including sheath and leader components according to one embodiment.

FIG. 3B is a top view of an endoscope 118 including sheath and leader components according to one embodiment. The endoscope 118 includes a leader 315 tubular component nested or partially nested inside and longitudinally-aligned with a sheath 311 tubular component. The sheath 311 includes a proximal sheath section 312 and distal sheath section 313. The leader 315 has a smaller outer diameter than the sheath 311 and includes a proximal leader section 316 and distal leader section 317. The sheath base 314 and the leader base 318 actuate the distal sheath section 313 and the distal leader section 317, respectively, for example, based on control signals from a user of a surgical robotic system 100. The sheath base 314 and the leader base 318 are, e.g., part of the IDM 117 shown in FIG. 1. The construction, composition, capabilities, and use of distal leader section 317, which may also be referred to as a flexure section, are disclosed in U.S. patent application Ser. No. 14/201,610, filed Mar. 7, 2014, and U.S. patent application Ser. No. 14/479,095, filed Sep. 5, 2014, the entire contents of which are incorporated by reference.

Both the sheath base 314 and the leader base 318 include drive mechanisms (e.g., the independent drive mechanism further described with reference to FIG. 4A-D in Section III. D. Instrument Device Manipulator) to control pull wires coupled to the sheath 311 and leader 315. For example, the sheath base 314 generates tensile loads on pull wires coupled to the sheath 311 to deflect the distal sheath section 313. Similarly, the leader base 318 generates tensile loads on pull wires coupled to the leader 315 to deflect the distal leader section 317. Both the sheath base 314 and leader base 318 may also include couplings for the routing of pneumatic pressure, electrical power, electrical signals, or optical signals from IDMs to the sheath 311 and leader 314, respectively. A pull wire may include a steel coil pipe along the length of the pull wire within the sheath 311 or the leader 315, which transfers axial compression back to the origin of the load, e.g., the sheath base 314 or the leader base 318, respectively.

The endoscope 118 can navigate the anatomy of a patient with ease due to the multiple degrees of freedom provided by pull wires coupled to the sheath 311 and the leader 315. For example, four or more pull wires may be used in either the sheath 311 and/or the leader 315, providing eight or more degrees of freedom. In other embodiments, up to three pull wires may be used, providing up to six degrees of freedom. The sheath 311 and leader 315 may be rotated up to 360 degrees along a longitudinal axis 306, providing more degrees of motion. The combination of rotational angles and multiple degrees of freedom provides a user of the surgical robotic system 100 with a user friendly and instinctive control of the endoscope 118.

III. A. Endoscope Sheath

Figure 3C:
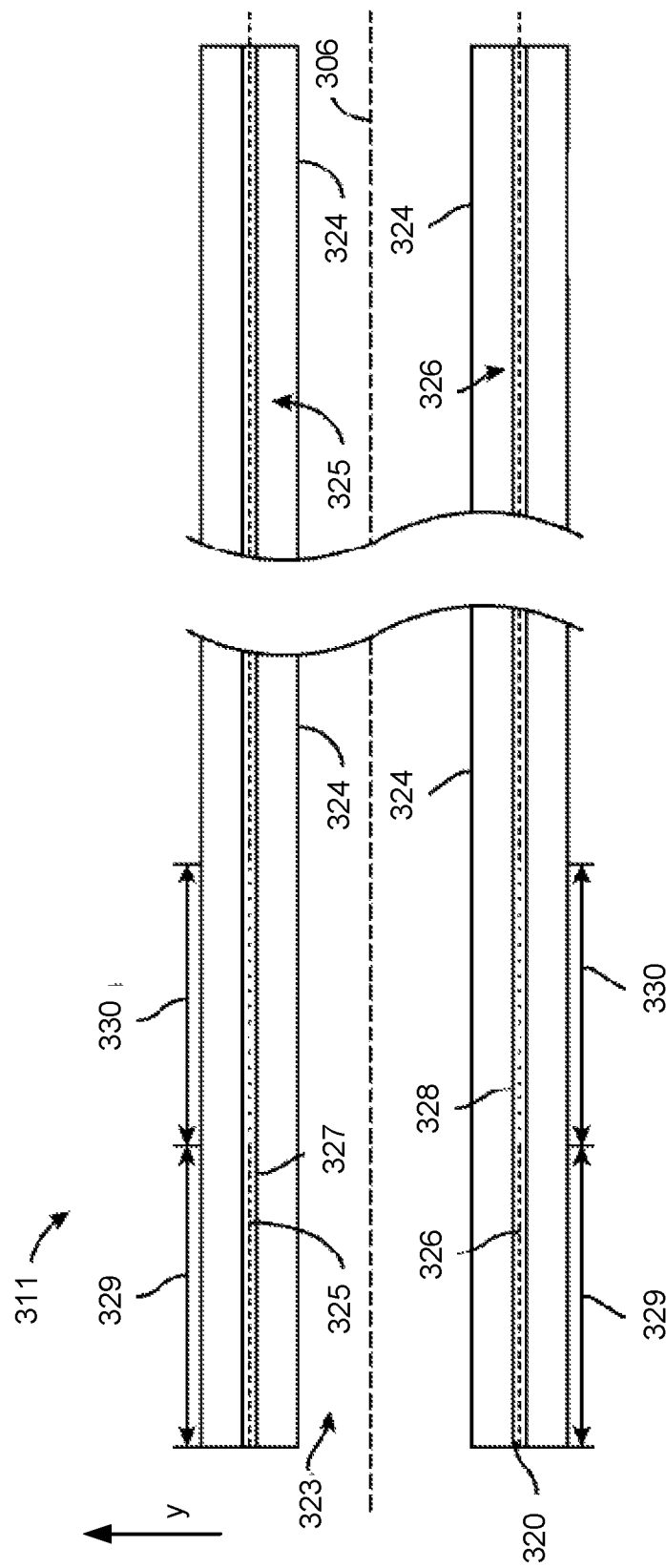
FIG. 3C is a cross sectional side view of a sheath of an endoscope according to one embodiment.

FIG. 3C is a cross sectional side view of the sheath 311 of the endoscope 118 according to one embodiment. The sheath 311 includes a lumen 323 sized to accommodate a tubular component such as the leader 315 shown in FIG. 3B. The sheath 311 includes walls 324 with pull wires 325 and 326 running through conduits 327 and 328 inside the length of walls 324. The conduits include a helix section 330 and a distal non-helix section 329. Appropriate tensioning of pull wire 325 may compress the distal end 320 in the positive y-axis direction, while minimizing bending of the helix section 330. Similarly, appropriate tensioning of pull wire 326 may compress distal end 320 in the negative y-axis direction. In some embodiments, the lumen 323 is not concentric with the sheath 311.

Pull wires 325 and 326 do not necessarily run straight through the length of sheath 311. Rather, the pull wires 325 and 326 spiral around sheath 311 along helix section 330 and run longitudinally straight (i.e., approximately parallel to the longitudinal axis 306) along the distal non-helix section 329 and any other non-helix section of the sheath 311. The helix section 330 may start and end anywhere along the length of the sheath 311. Further, the length and pitch of helix section 330 may be determined based on desired properties of sheath 311, e.g., flexibility of the sheath 311 and friction in the helix section 330.

Though the pull wires 325 and 326 are positioned at 180 degrees relative to each other in FIG. 3C, it should be noted that pull wires of the sheath 311 may be positioned at different angles. For example, three pull wires of a sheath may each be positioned at 120 degrees relative to each other. In some embodiments, the pull wires are not equally spaced relative to each other, i.e., without a constant angle offset.

III. B. Helix Sections

Figure 3D:
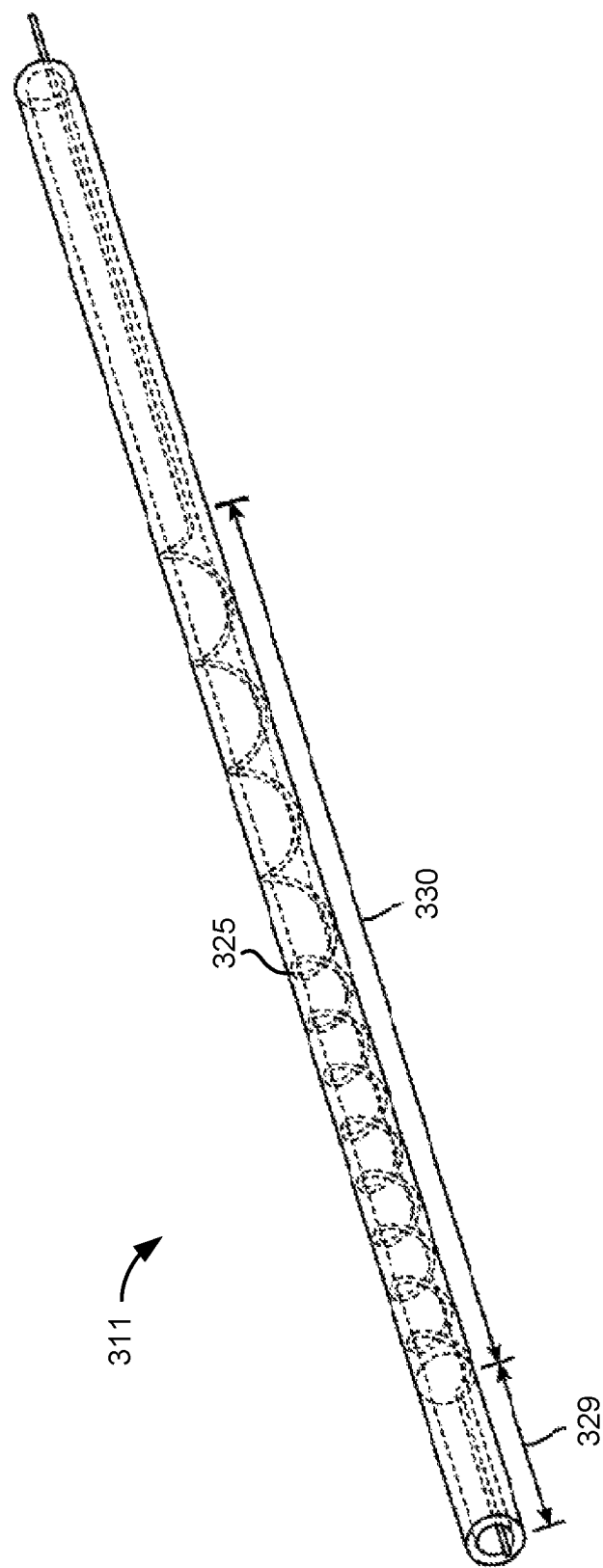
FIG. 3D is an isometric view of a helix section of a sheath of an endoscope according to one embodiment.

FIG. 3D is an isometric view of a helix section 330 of the sheath 311 of the endoscope 118 according to one embodiment. FIG. 3D shows only one pull wire 325 for the purpose of distinguishing between the distal non-helix section 329 and the helix section 330. In some embodiments, the helix section 330 has a variable pitch.

Figure 3E:
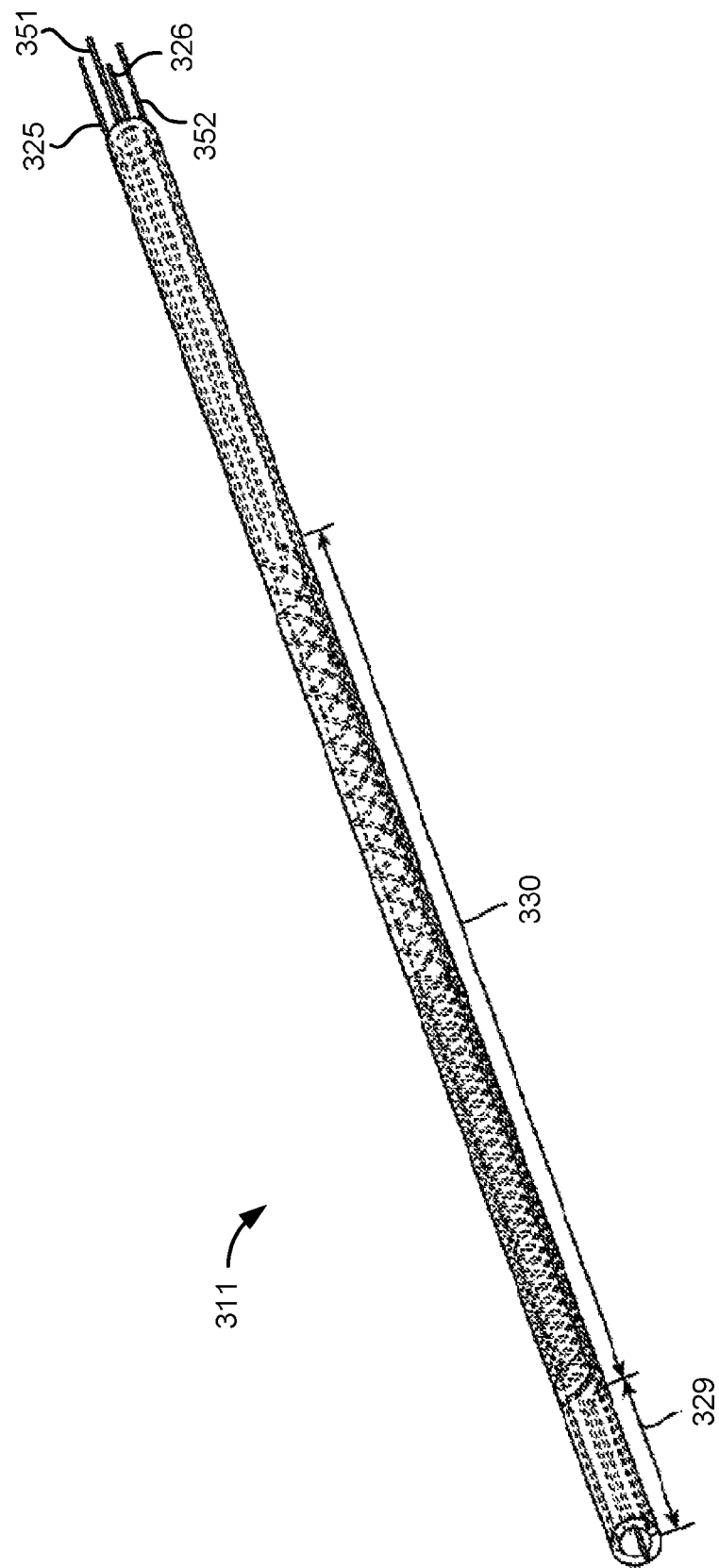
FIG. 3E is another isometric view of a helix section of a sheath of an endoscope according to one embodiment.

FIG. 3E is another isometric view of a helix section 330 of a sheath 311 of an endoscope 118 according to one embodiment. FIG. 3E shows four pull wires 325, 326, 351, and 352 extending along the distal non-helix section 329 and the variable pitch helix section 330.

Helix sections 330 in the sheath 311 and leader 315 of the endoscope 118 help a surgical robotic system 100 and/or a user navigate the endoscope 118 through non-linear pathways in the anatomy of a patient, e.g., intestines or the colon. When navigating the non-linear pathways, it is useful for the endoscope 118 to remain flexible, while still having a controllable distal section (in both the sheath 311 and the leader 315). Further, it is advantageous to reduce the amount of unwanted bending along the endoscope 118. In previous endoscope designs, tensioning the pull wires to manipulate the distal section generated the unwanted bending and torquing along a length of the endoscope, which may be referred to as muscling and curve alignment, respectively.

FIG. 3F is a side view of the sheath 311 of the endoscope 118 with a helix section 330 according to one embodiment. FIGS. 3F-G illustrate how the helix section 330 helps substantially mitigate muscling and curve alignment. Since the pull wire 325 is spiraled around the length of helix section 330, the pull wire 325 radially and symmetrically distributes a compressive load 335 in multiple directions around the longitudinal axis 306. Further, bending moments imposed on the endoscope 118 are also symmetrically distributed around the longitudinal axis 306, which counterbalances and offsets opposing compressive forces and tensile forces. The distribution of the bending moments results in minimal net bending and rotational forces, creating a low potential energy state of the endoscope 118, and thus eliminating or substantially mitigating muscling and curve alignment.

The pitch of the helix section 330 can affect the friction and the stiffness of the helix section 330. For example, the helix section 330 may be shorter to allow for a longer distal non-helix section 329, resulting in less friction and/or stiffness of the helix section 330.

FIG. 3G is another view of the sheath 311 of the endoscope 118 shown in FIG. 3F according to one embodiment. Compared to the distal non-helix section 329 shown in FIG. 3F, the distal non-helix section 329 shown in FIG. 3G is deflected at a greater angle.

III. C. Endoscope Leader

Figure 3H:
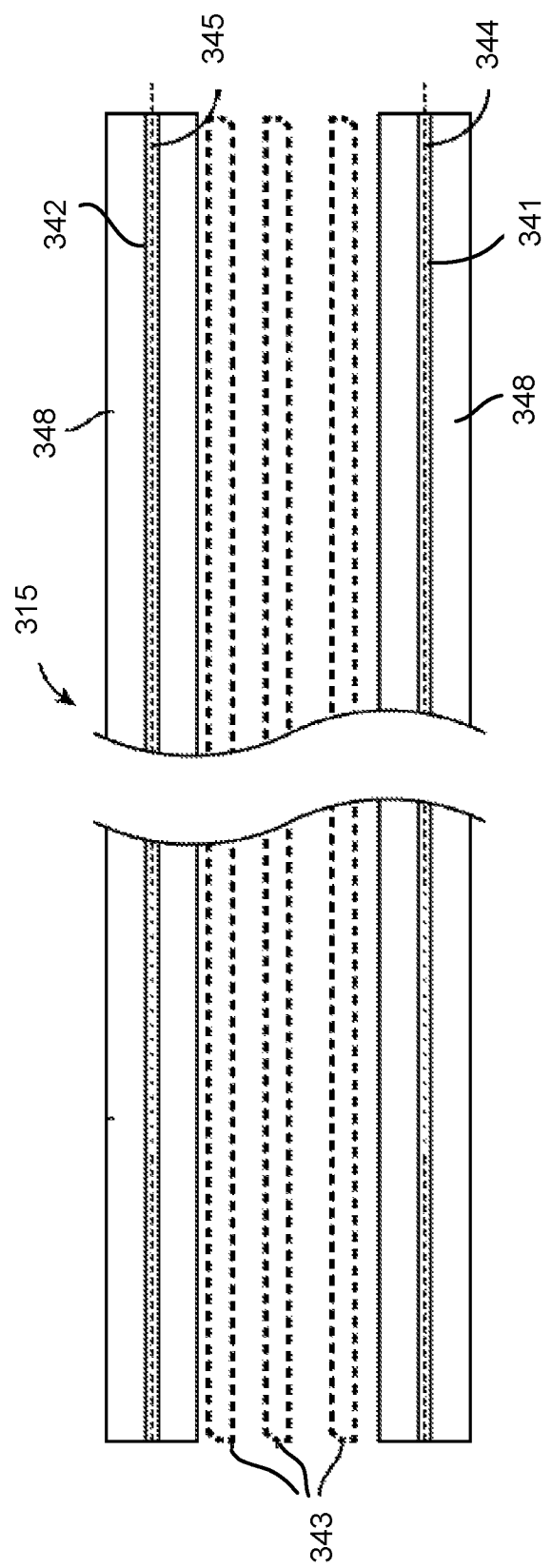
FIG. 3H is a cross sectional side view of a leader of an endoscope according to one embodiment.

FIG. 3H is a cross sectional side view of the leader 315 of the endoscope 118 according to one embodiment. The leader 315 includes at least one working channel 343 and pull wires 344 and 345 running through conduits 341 and 342, respectively, along the length of the walls 348. The pull wires 344 and 345 and conduits 341 and 342 are substantially the same as the pull wires 325 and 326 and the conduits 327 and 328 in FIG. 3C, respectively. For example, the pull wires 344 and 345 may have a helix section that helps mitigate muscling and curve alignment of the leader 315, similar to the sheath 311 as previously described.

Figure 3I:
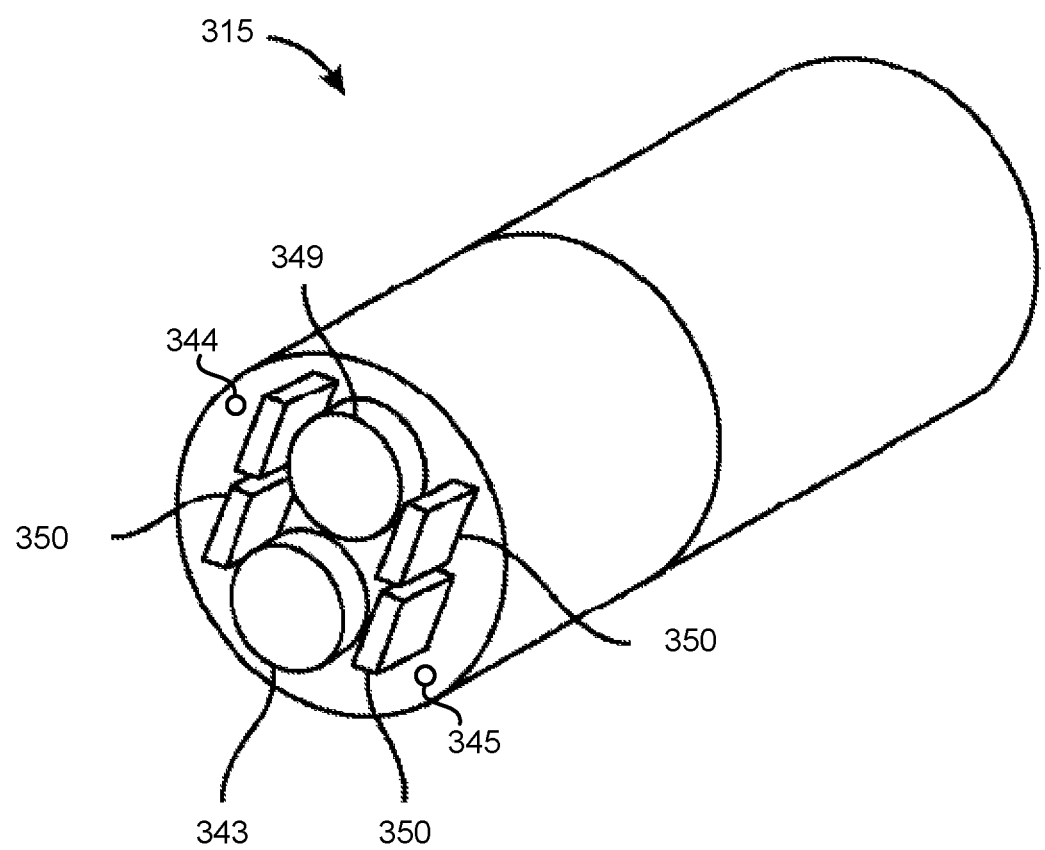
FIG. 3I is a cross sectional isometric view of a distal tip of the leader of the endoscope shown in FIG. 3H according to one embodiment.

FIG. 3I is a cross sectional isometric view of a distal tip of the leader 315 of the endoscope 118 shown in FIG. 3H according to one embodiment. The leader 315 includes an imaging device 349 (e.g., charge-coupled device (CCD) or complementary metal-oxide semiconductor (CMOS) camera, imaging fiber bundle, etc.), light sources 350 (e.g., light-emitting diode (LED), optic fiber, etc.), at least two pull wires 344 and 345, and at least one working channel 343 for other components. For example, other components include camera wires, an insufflation device, a suction device, electrical wires, fiber optics, an ultrasound transducer, electromagnetic (EM) sensing components, and optical coherence tomography (OCT) sensing components. In some embodiments, the leader 315 includes a pocket hole to accommodate insertion of a component into a working channel 343. As shown in FIG. 3I, the pull wires 344 and 345 are not concentric with the an imaging device 349 or the working channel 343.

III. D. Instrument Device Manipulator

Figure 4A:
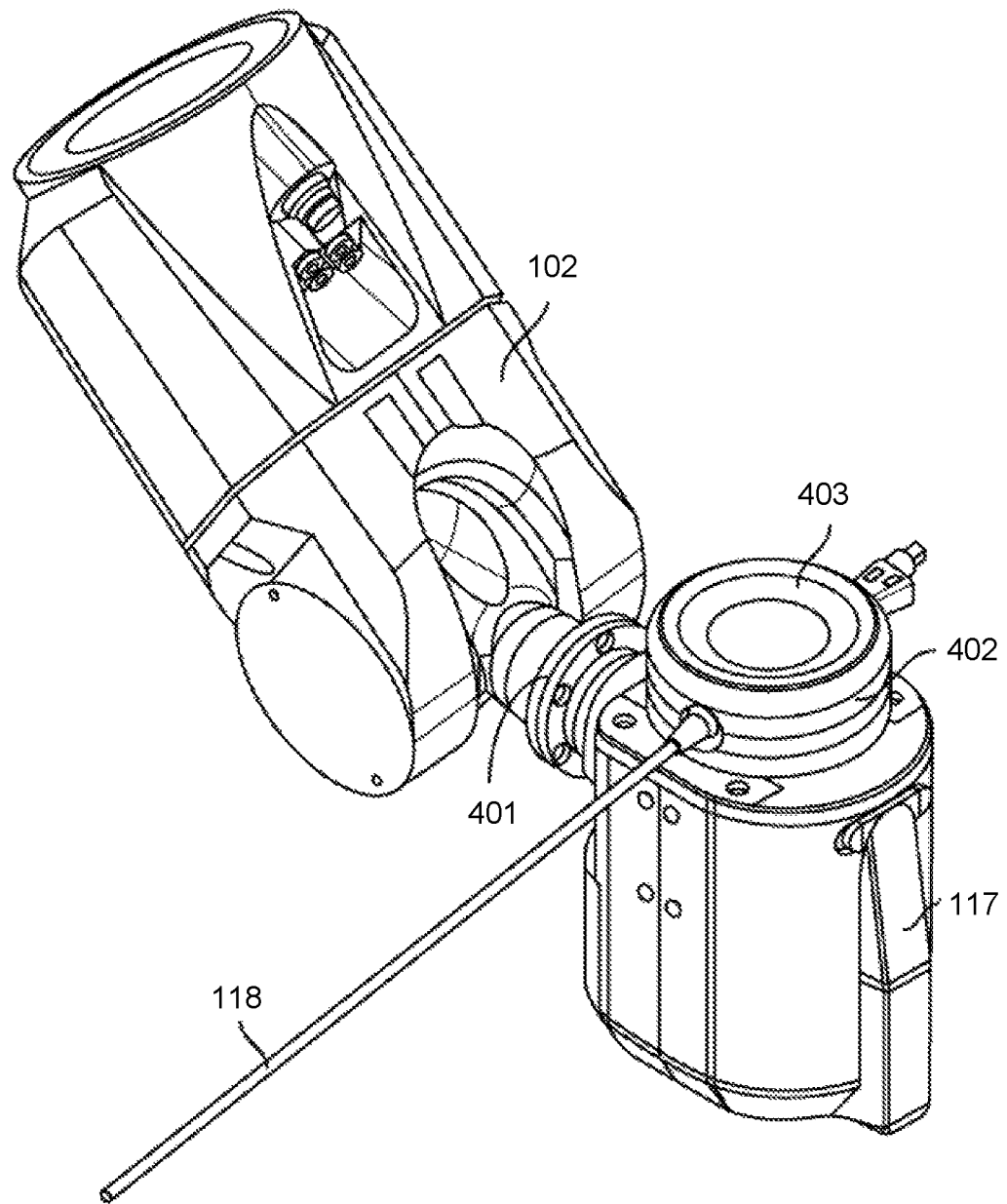
FIG. 4A is an isometric view of an instrument device manipulator of a surgical robotic system according to one embodiment.

FIG. 4A is an isometric view of an instrument device manipulator 117 of the surgical robotic system 100 according to one embodiment. The robotic arm 102 is coupled to the IDM 117 via an articulating interface 401. The IDM 117 is coupled to the endoscope 118. The articulating interface 401 may transfer pneumatic pressure, power signals, control signals, and feedback signals to and from the robotic arm 102 and the IDM 117. The IDM 117 may include a gear head, motor, rotary encoder, power circuits, and control circuits. A tool base 403 for receiving control signals from the IDM 117 is coupled to the proximal end of the endoscope 118. Based on the control signals, the IDM 117 manipulates the endoscope 118 by actuating output shafts, which are further described below with reference to FIG. 4B.

Figure 4B:
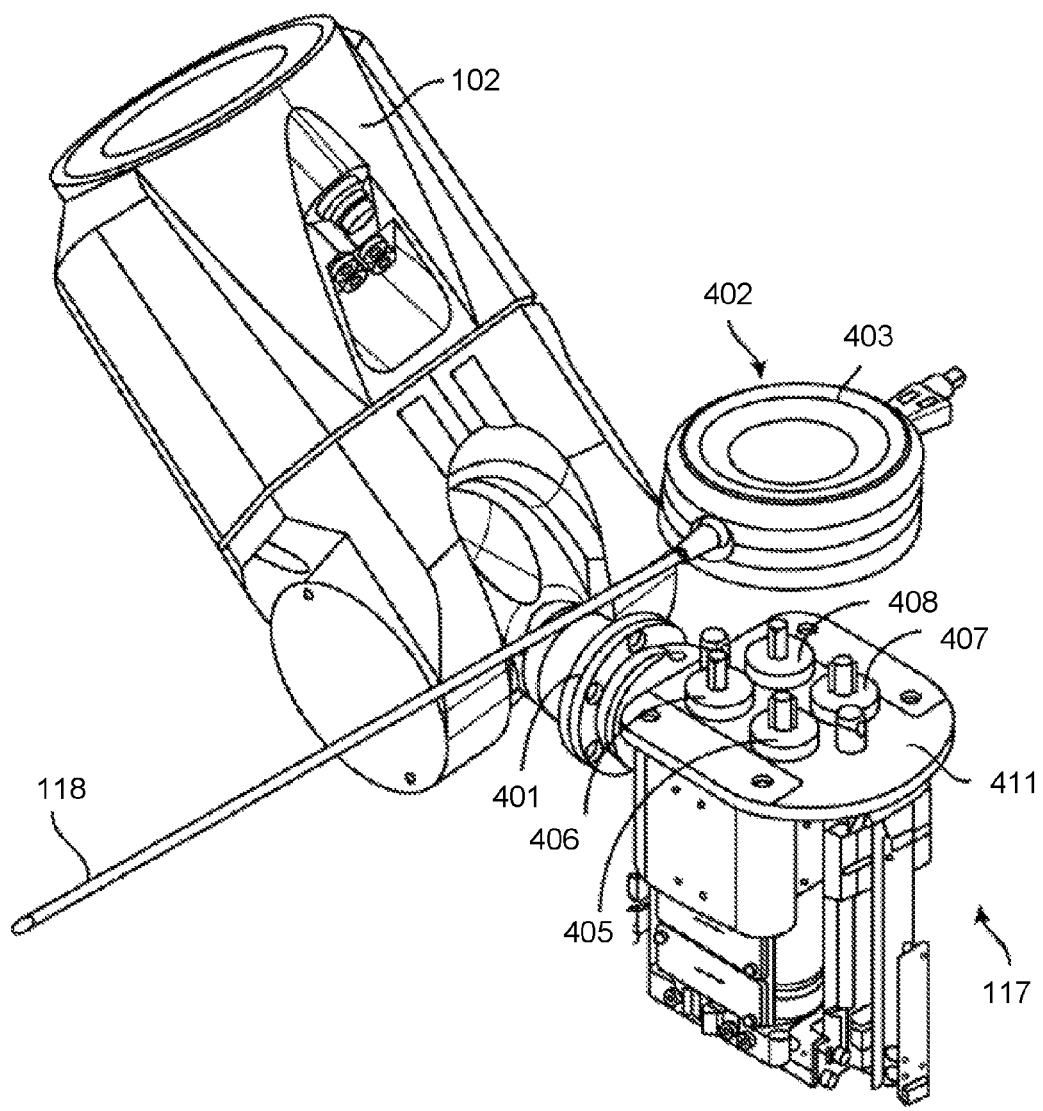
FIG. 4B is an exploded isometric view of the instrument device manipulator shown in FIG. 4A according to one embodiment.

FIG. 4B is an exploded isometric view of the instrument device manipulator shown in FIG. 4A according to one embodiment. In FIG. 4B, the endoscopic 118 has been removed from the IDM 117 to reveal the output shafts 405, 406, 407, and 408.

Figure 4C:
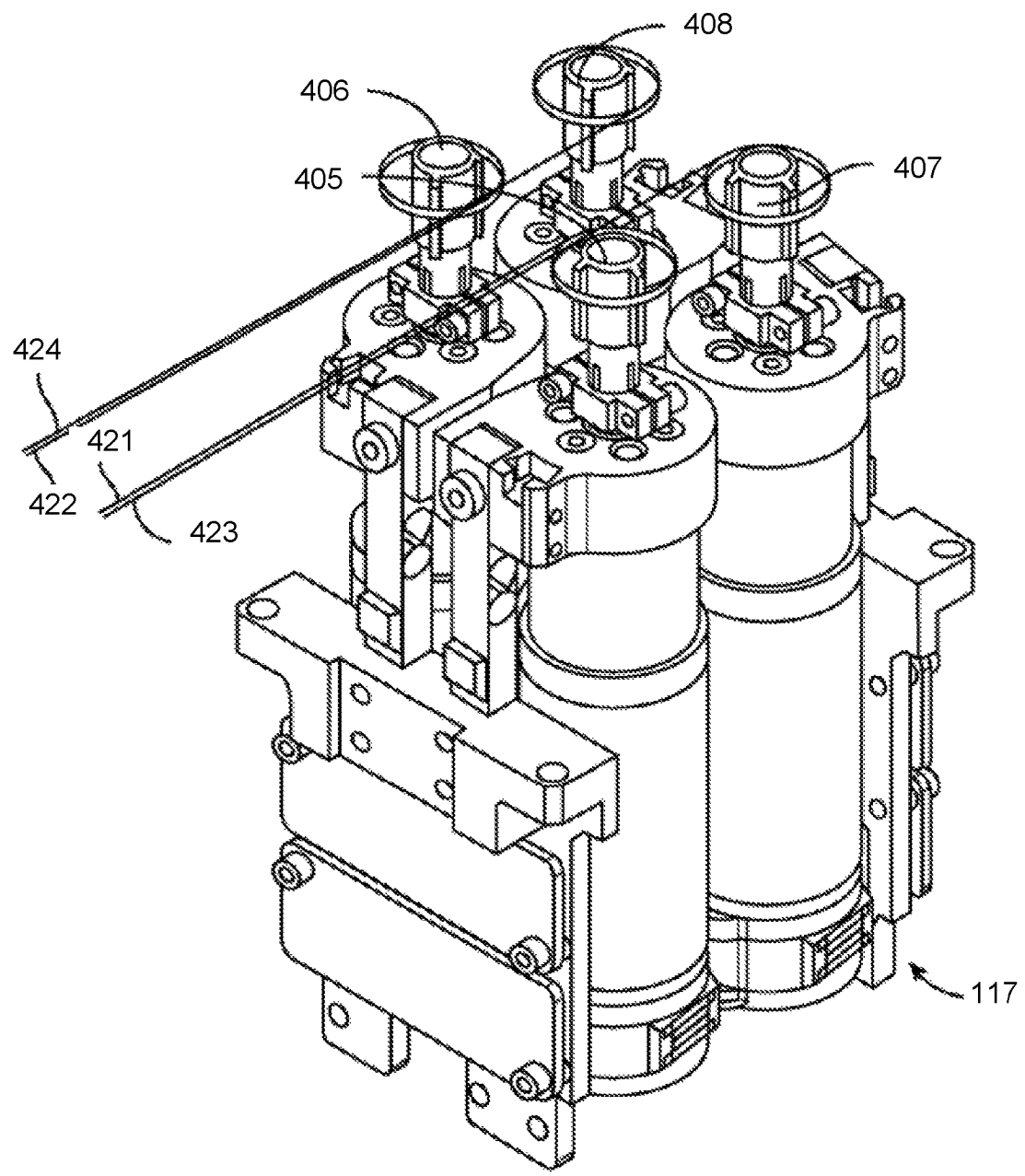
FIG. 4C is an isometric view of an independent drive mechanism of the instrument device manipulator shown in FIG. 4A according to one embodiment.

FIG. 4C is an isometric view of an independent drive mechanism of the instrument device manipulator 117 shown in FIG. 4A according to one embodiment. The independent drive mechanism can tighten or loosen the pull wires 421, 422, 423, and 424 (e.g., independently from each other) of an endoscope by rotating the output shafts 405, 406, 407, and 408 of the IDM 117, respectively. Just as the output shafts 405, 406, 407, and 408 transfer force down pull wires 421, 422, 423, and 424, respectively, through angular motion, the pull wires 421, 422, 423, and 424 transfer force back to the output shafts. The IDM 117 and/or the surgical robotic system 100 can measure the transferred force using a sensor, e.g., a strain gauge further described below.

Figure 4D:
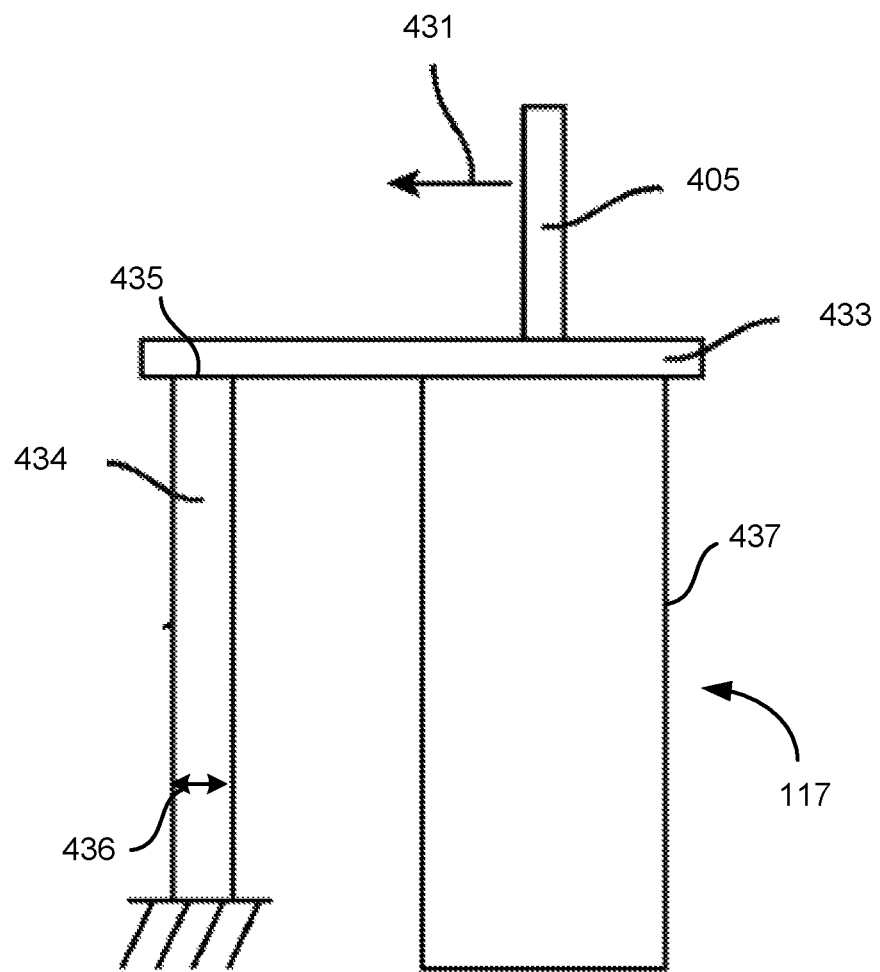
FIG. 4D illustrates a conceptual diagram that shows how forces may be measured by a strain gauge of the independent drive mechanism shown in FIG. 4C according to one embodiment.

FIG. 4D illustrates a conceptual diagram that shows how forces may be measured by a strain gauge 434 of the independent drive mechanism shown in FIG. 4C according to one embodiment. A force 431 may directed away from the output shaft 405 coupled to the motor mount 433 of the motor 437. Accordingly, the force 431 results in horizontal displacement of the motor mount 433. Further, the strain gauge 434 horizontally coupled to the motor mount 433 experiences strain in the direction of the force 431. The strain may be measured as a ratio of the horizontal displacement of the tip 435 of strain gauge 434 to the overall horizontal width 436 of the strain gauge 434.

In some embodiments, the IDM 117 includes additional sensors, e.g., inclinometers or accelerometers, to determine an orientation of the IDM 117. Based on measurements from the additional sensors and/or the strain gauge 434, the surgical robotic system 100 can calibrate readings from the strain gauge 434 to account for gravitational load effects. For example, if the IDM 117 is oriented on a horizontal side of the IDM 117, the weight of certain components of the IDM 117 may cause a strain on the motor mount 433. Accordingly, without accounting for gravitational load effects, the strain gauge 434 may measure strain that did not result from strain on the output shafts.

IV. Unideal Endoscope Motion

Figure 5A:
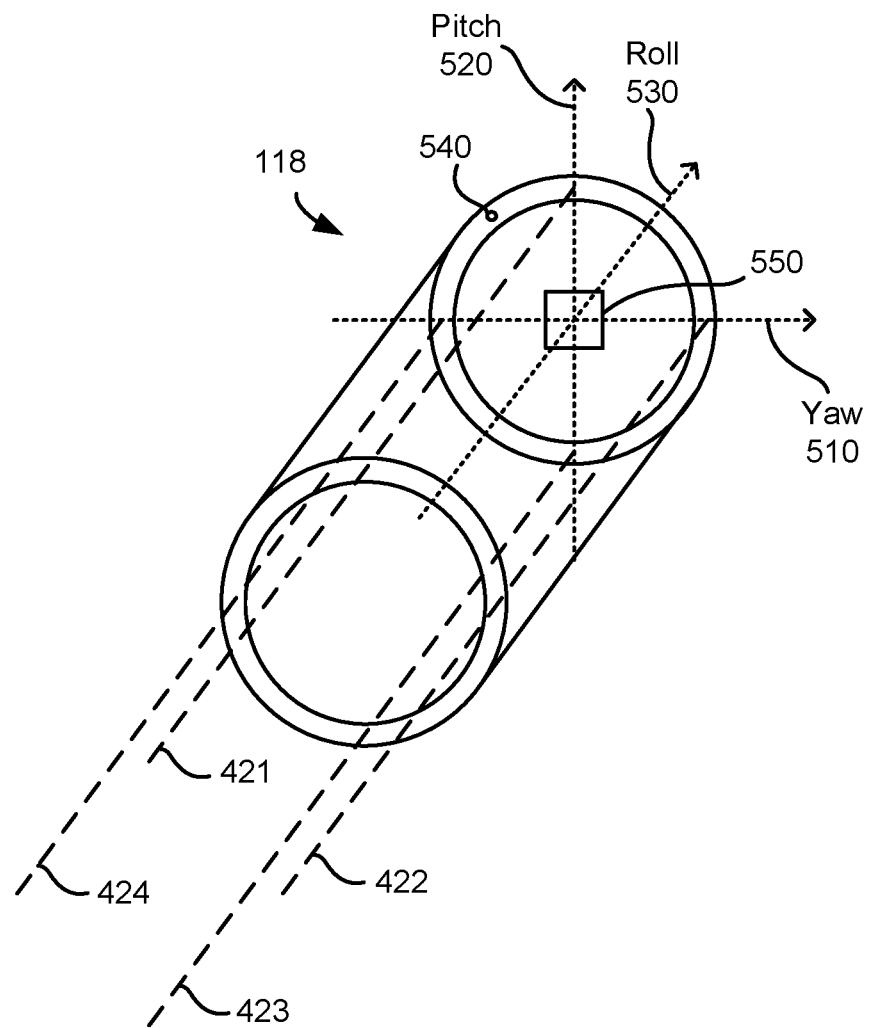
FIG. 5A illustrates pull wires inside an endoscope according to one embodiment.

FIG. 5A illustrates pull wires inside the endoscope 118 according to one embodiment. The endoscope 118 may include a different number of pull wires depending upon the construction of the endoscope, but for sake of example the following description assumes a construction where the endoscope 118 includes the four pull wires 421, 422, 423, and 423 each a corresponding to a direction of movement along the yaw 510 and pitch 520 axis. In particular, pulling the pull wires 421, 422, 423, and 423 moves the endoscope 118 in the positive pitch direction, positive yaw direction, negative pitch direction, and negative yaw direction, respectively. Though the pull wires shown in FIG. 5A are each aligned to a yaw 510 or pitch 520 direction, in other embodiments, the pull wires may not necessarily be aligned along these axes, the axes above are arbitrarily chosen for convenience of explanation. For example, a pull wire may be aligned with (e.g., intersect) the point 540 in the endoscope 118. Thus, translating the pull wire would cause the endoscope 118 to move in both the yaw 510 and pitch 520 directions. In the example embodiment described throughout, when the endoscope 118 is in a resting position the pull wires are approximately parallel with the roll 530 axis.

The endoscope 118 may include one or more spatial sensors 550 coupled toward the distal tip of the endoscope 118. The spatial sensors 550 can be, for example, an electromagnetic (EM) sensor, accelerometer, gyroscope, fiducial marker, and/or other types of sensors. In one embodiment, the spatial sensor 550 is a shape sensing optical fiber embedded inside the endoscope 118 and running along a length of the endoscope 118. The spatial sensors 550 may provide spatial data indicating a position and/or orientation of the endoscope 118, e.g., in real-time. Spatial data may also be used as calibration data to assist in calibration of the endoscope 118.

In an ideal endoscope, translating pull wires of the endoscope moves the endoscope exactly to a target position or orientation, e.g., bend the tip of the endoscope 90 degrees in the positive pitch direction. However, in practice, due to imperfections of the endoscope, the target motion does not necessarily match the actual motion of the endoscope, and the endoscope may exhibit nonlinear behavior. Imperfections may arise for a variety of reasons, examples of which may be the result of defects in manufacturing (e.g., a pull wire is not properly aligned with an axis of motion), variances in the pull wires (e.g., a pull wire is more stiff, or different in length, than another pull wire), or variances in the endoscope material (e.g., the pitch direction bends more easily than the yaw direction).

IV. A. Unideal Offset in Pitch Direction

Figure 5B:
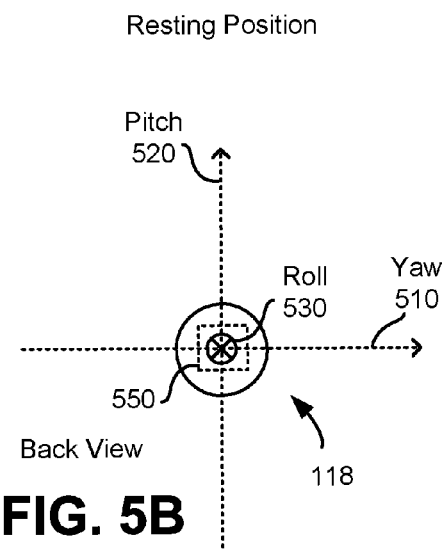
FIG. 5B shows a back view of an endoscope in a resting position according to one embodiment.
Figure 5C:
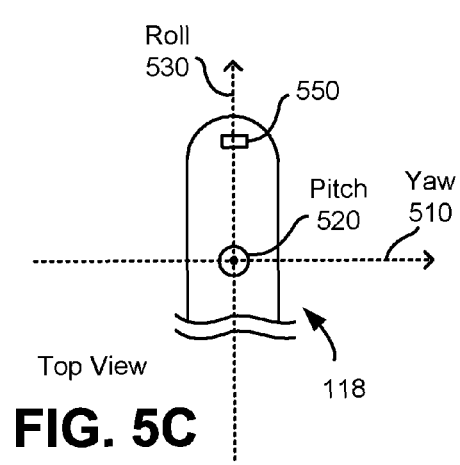
FIG. 5C shows a top view of the endoscope shown in FIG. 5B according to one embodiment.
Figure 5D:
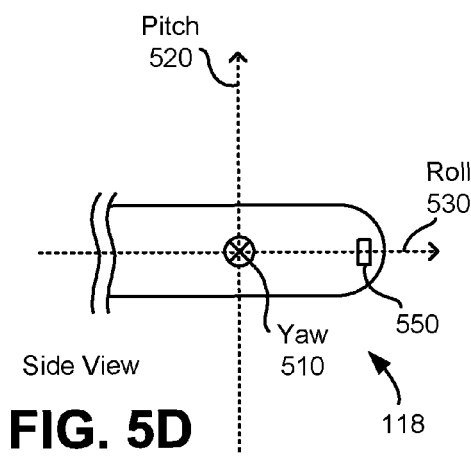
FIG. 5D shows a side view of the endoscope shown in FIG. 5B according to one embodiment.
Figure 5E:
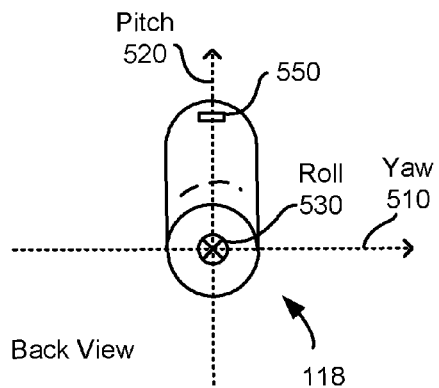
FIG. 5E shows a back view of the endoscope shown in FIG. 5B in a deflected position according to one embodiment.
Figure 5F:
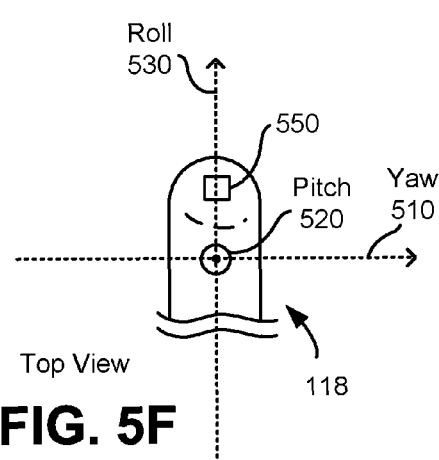
FIG. 5F shows a top view of the endoscope shown in FIG. 5E according to one embodiment.
Figure 5G:
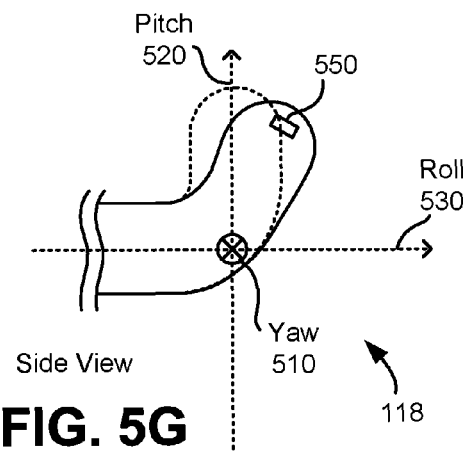
FIG. 5G shows a side view of the endoscope shown in FIG. 5E according to one embodiment.

FIGS. 5B-5D illustrate three views of an endoscope 118 in a resting position. FIGS. 5E-G illustrate the same three views after the endoscope 118 has been moved to a deflected position in response to a command to articulate to a target deflection of 90 degrees in the positive pitch 520 direction. As shown in FIGS. 5E-G, the actual deflection of the endoscope 118 exhibits an unideal offset in the positive pitch 520 direction.

FIG. 5B shows a back view of the endoscope 118 in a resting position according to one embodiment. In the back view, a viewer is looking down from the proximal end of the endoscope, where the opposite distal end would be inserted into a body of a patient. The cross section of the endoscope 118 is aligned to the origin of the yaw 510 and pitch 520 axis. The endoscope 118 is parallel to the roll 530 axis, and a spatial sensor 550 is coupled toward the tip of the endoscope 118. FIG. 5C shows a top view of the endoscope 118 shown in FIG. 5B according to one embodiment. As an illustrative example, a patient is lying horizontally flat on a table for a surgical procedure. The endoscope 118 is positioned to be parallel to the body of the patient, and the surgical robotic system 100 inserts the endoscope 118 into the body while maintaining the parallel configuration. In the top view, a viewer is looking down from above the body of the patient. FIG. 5D shows a side view of the endoscope 118 shown in FIG. 5B according to one embodiment.

FIG. 5E shows a back view of the endoscope 118 shown in FIG. 5B in the deflected position according to one embodiment. FIG. 5F shows a top view of the endoscope 118 shown in FIG. 5E according to one embodiment. FIG. 5G shows a side view of the endoscope 118 shown in FIG. 5E according to one embodiment. The dotted outline of the endoscope 118 indicates the target deflected position that the endoscope should have moved to in response to the command, e.g., the tip of the endoscope 118 is supposed deflect 90 degrees in the positive pitch direction to become parallel to the pitch 520 axis. However, the actual deflected position is short of a 90 degree deflection, and thus exhibits the unideal offset in the positive pitch 520 direction.

IV. B. Unideal Offset in Yaw Direction

Figure 5H:
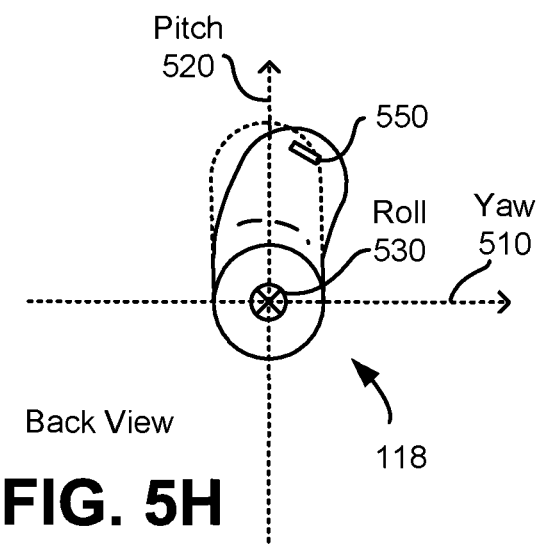
FIG. 5H shows a back view of the endoscope shown in FIG. 5B in a deflected position with an additional unideal offset according to one embodiment.

FIG. 5H shows a back view of the endoscope 118 shown in FIG. 5B in a deflected position with an additional unideal offset according to one embodiment. In particular, in addition to the unideal offset in the positive pitch 520 direction, the endoscope shown in FIG. 5H exhibits an additional unideal offset in the positive yaw 510 direction. Thus, the distal end (e.g., tip) of the endoscope 118 is "curved," in contrast to the distal end of the endoscope shown in FIG. 5F that is "straight." The endoscope 118 shown in FIG. 5H has imperfections in two directions (positive pitch and yaw), however, in other embodiments, endoscopes can exhibit imperfections in any number of directions (e.g., negative pitch and yaw, as well as roll).

Figure 5I:
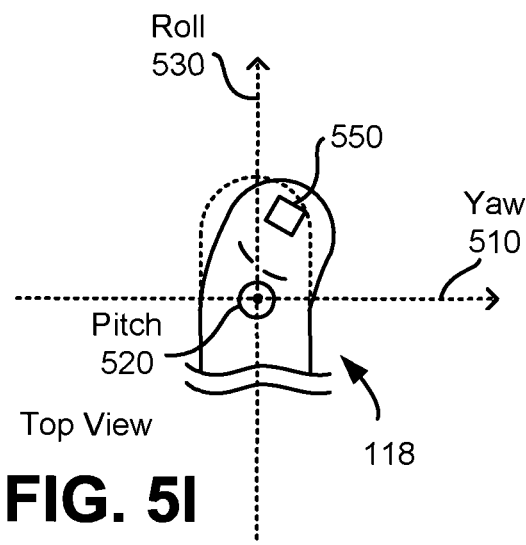
FIG. 5I shows a top view of the endoscope shown in FIG. 5H according to one embodiment.

FIG. 5I shows a top view of the endoscope 118 shown in FIG. 5H according to one embodiment.

IV. C. Unideal Offset in Roll Direction

Figure 5J:
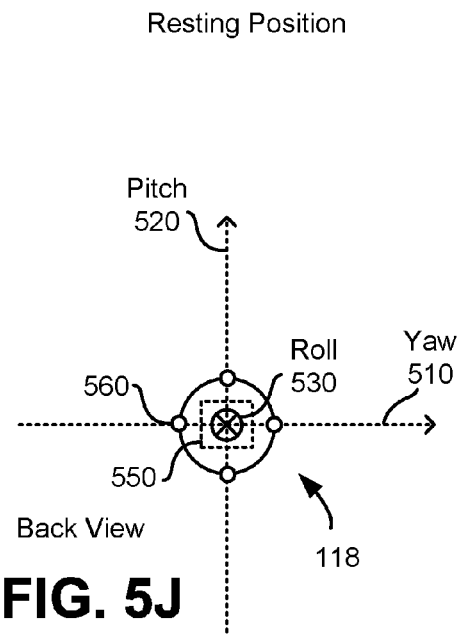
FIG. 5J shows a back view of the endoscope shown in FIG. 5B in a resting position according to one embodiment.
Figure 5K:
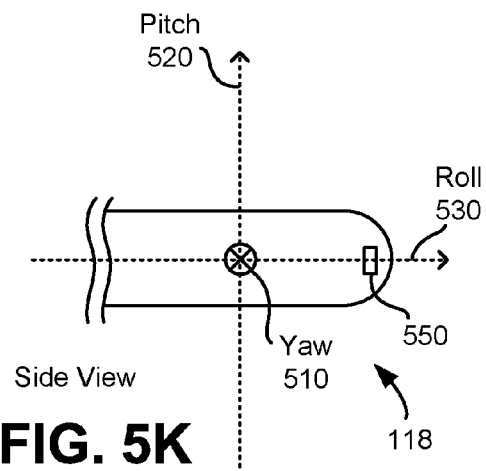
FIG. 5K shows a side view of the endoscope shown in FIG. 5J according to one embodiment.

FIGS. 5J-5K illustrate two views of an endoscope 118 in a resting position. Four markers 560 are shown on the endoscope 118 for purposes of illustrating the alignment of the endoscope 118 relative to the yaw 510 and pitch 520 directions. In the resting position, each of the markers are aligned with the yaw 510 and pitch 520 axis.

Figure 5L:
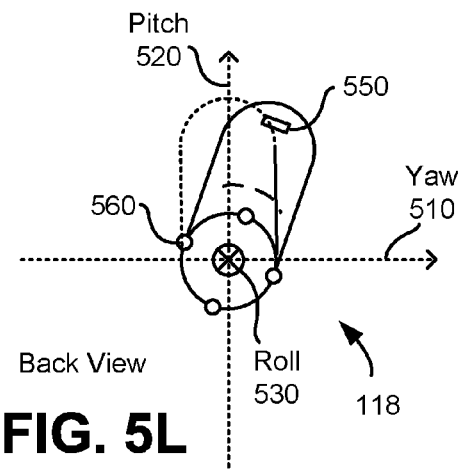
FIG. 5L shows a back view of the endoscope shown in FIG. 5J in a deflected position with an additional unideal roll offset according to one embodiment.
Figure 5M:
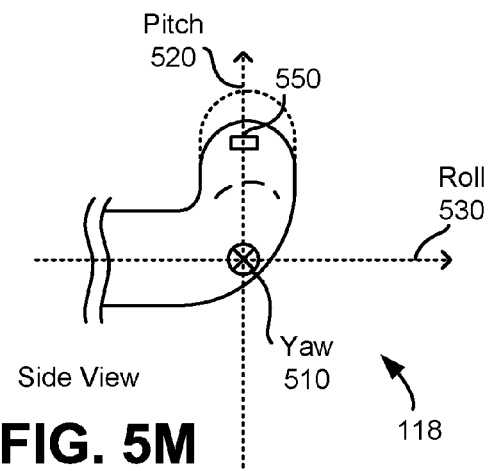
FIG. 5M shows a side view of the endoscope shown in FIG. 5L according to one embodiment.

FIGS. 5L-M illustrate the same two views after the endoscope 118 has been moved to a deflected position in response to a command to articulate to a target deflection of 90 degrees in the positive pitch 520 direction. As shown in FIGS. 5L-M, the actual deflection of the endoscope 118 exhibits an unideal offset in the roll 530 direction (and no other unideal offsets in this example). The dotted outline of the endoscope 118 indicates the target deflected position that the endoscope should have moved to in response to the command, e.g., the tip of the endoscope 118 is supposed deflect 90 degrees to become parallel to the pitch 520 axis. The actual deflected position has a deflection 90 degrees, but also has a rotation along the roll 530 axis. Thus, the four markers 560 are no longer aligned with the yaw 510 and pitch 520 axis. Similar to the endoscope shown in FIG. 5E, the distal end of the endoscope in FIG. 5L is "straight" and not "curved." In some embodiments, rotation of the proximal end of an endoscope is accompanied by corresponding rotation of the distal end of the endoscope (and vice versa). The rotations may be equal or different, e.g., a 10 degree roll offset of the proximal end causes a 20 degree roll offset of the distal end. As another example, there may be no roll offset at the proximal end, and a nonzero roll offset at the distal end.

FIG. 5M shows a side view of the endoscope shown in FIG. 5L according to one embodiment.

In summary, FIGS. 5B-G illustrate an unideal offset in the positive pitch direction, FIGS. 5H-I illustrate an unideal offset in the yaw direction in addition to in the positive pitch direction, and FIGS. 5J-M illustrate an unideal offset in the roll direction. In other embodiments, endoscopes may exhibit unideal offsets in any number or combination of directions. The magnitude of the offsets may vary between different directions.

V. Spatial Sensors

V. A. Electromagnetic Sensors

Figure 6A:
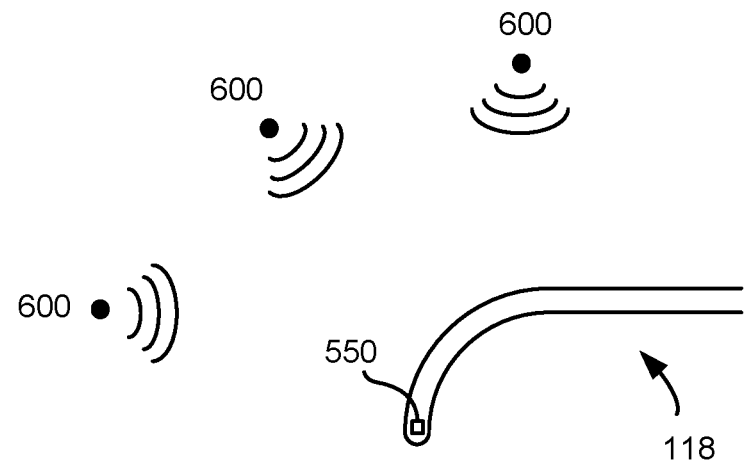
FIG. 6A is a diagram of an electromagnetic tracking system according to one embodiment.

FIG. 6A is a diagram of electromagnetic tracking system according to one embodiment. The spatial sensor 550 coupled to the tip of the endoscope 118 includes one or more EM sensors 550 that detect an electromagnetic field (EMF) generated by one or more EMF generators 600 in proximity to the endoscope 118. The strength of the detected EMF is a function of the position and/or orientation of the endoscope 118. If the endoscope 118 includes more than one EM sensor 550, for example, a first EM sensor is coupled to a leader tubular component and a second EM sensor is coupled to a sheath tubular component of the endoscope 118.

One or more EMF generators 600 are located externally to a patient. The EMF generators 600 emit EM fields that are picked up by the EM sensor 550.

If multiple EMF generators 600 and/or EM sensors 550 are used, they may be modulated in a number of different ways so that when their emitted/received fields are processed by the computer system 120 (or any computer system external to the surgical robotic system 100), the signals are separable. Thus, the computer system 120 can process multiple signals (sent and/or received) each as a separate input providing separate triangulation location regarding the location of the EM sensor/s 550, and by extension the position of the endoscope 118. For example, multiple EMF generators 600 may be modulated in time or in frequency, and may use orthogonal modulations so that each signal is fully separable from each other signal (e.g., using signal processing techniques such as filtering and Fourier Transforms) despite possibly overlapping in time. Further, the multiple EM sensors 550 and/or EMF generators 600 may be oriented relative to each other in Cartesian space at non-zero, non-orthogonal angles so that changes in orientation of the EM sensor/s 550 will result in at least one of the EM sensor/s 550 receiving at least some signal from the one or more EMF generators 600 at any instant in time. For example, each EMF generator 600 may be, along any axis, offset at a small angle (e.g., 7 degrees) from each of two other EM generators 600 (and similarly with multiple EM sensors 550s). As many EMF generators or EM sensors as desired may be used in this configuration to assure accurate EM sensor position information along all three axes and, if desired, at multiple points along the endoscope 118.

V. B. Camera Sensors

Figure 6B:
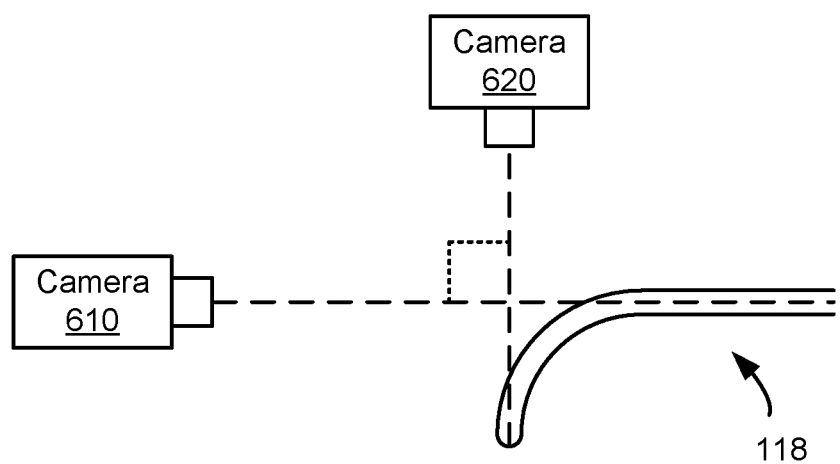
FIG. 6B is a diagram of cameras in proximity to an endoscope according to one embodiment.

FIG. 6B is a diagram of cameras in proximity to an endoscope 118 according to one embodiment. The cameras may include any type of optical cameras such as digital video cameras, stereo cameras, high-speed cameras, light field cameras, etc. A first camera 610 is parallel to a longitudinal axis of the endoscope 118. A second camera 620 is orthogonal to the first camera 610. Since the cameras each capture image frames showing the position and/or orientation of the endoscope in at least two-dimensions, aligning the two cameras orthogonal to each other enables the surgical robotic system 100 to receive information about the endoscope in at least three-dimensions (e.g., corresponding to the pitch, yaw, and roll axis). In other embodiments, three or more cameras may be used to capture images of the endoscope 118. The data processing module 160 may implement object tracking image processing techniques using the captured image frames to determine the real-time 3D position of the endoscope 118. Example techniques include correlation-based matching methods, feature-based methods, and optical flow.

Figure 6C:
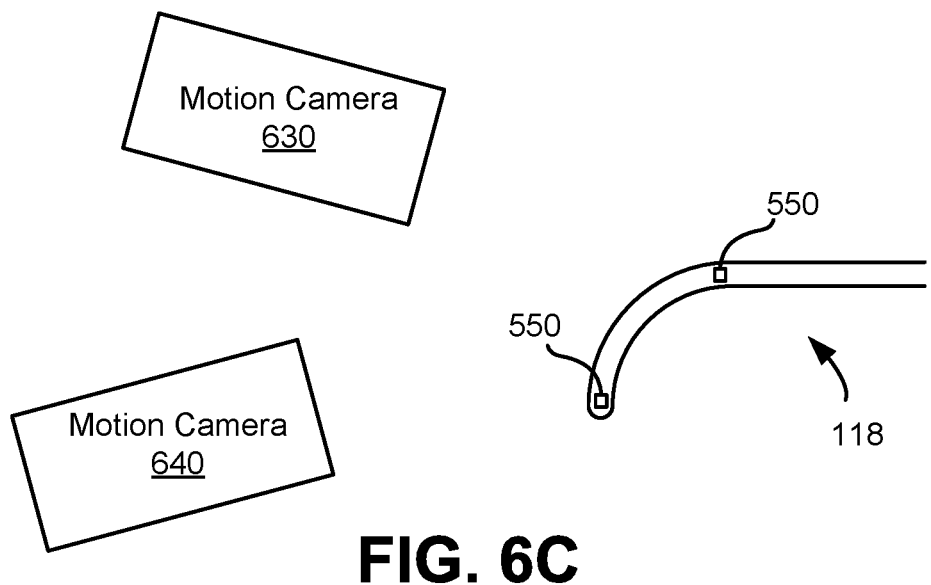
FIG. 6C is a diagram of motion tracking cameras in proximity to an endoscope including fiducial markers according to one embodiment.

FIG. 6C is a diagram of motion cameras in proximity to an endoscope 118 including fiducial markers according to one embodiment. The spatial sensors 550 coupled to toward the distal end of the endoscope 118 are fiducial markers. The motion cameras 630 and 640 capture image frames that track the position and movement of the fiducial markers. Though two fiducial markers and two motion cameras are shown in FIG. 6C, other embodiments may include any other number of fiducial markers coupled to the endoscope and/or motion cameras to track the fiducial markers.

In contrast to the cameras in FIG. 6B, the motion cameras in FIG. 6C capture data describing the motion of the fiducial markers. Thus, in some embodiments, the data processing module 160 requires less computational resources to process the motion camera data than to process data captured from other optical cameras without using fiducial markers. For example, other optical cameras capture data describing the visual appearance (e.g., color and size) of the endoscope 118. However, the motion cameras may only need to capture the real-time coordinate position of each fiducial marker, which is sufficient for the data processing module 160 to use to determine overall movement of the endoscope 118 in different directions (e.g., pitch, yaw, and roll) in response to commands from the surgical robotic system 100.

Camera based sensors may be more suitable for determining the position of an endoscope outside a body of a patient, while EM sensors may be more suitable for use cases where the endoscope is inside the body. In some embodiments, image processing techniques using camera data provide more accurate or higher resolution position and motion data than EM sensor based techniques, e.g., because a user viewing the endoscope outside of the body can validate the results of image processing techniques. In contrast, EM sensors have an advantage in that they can still detect EM fields generated by EMF generators even when the endoscope is located inside a patient.

V. C. Shape Sensing Optical Fiber

Figure 6D:
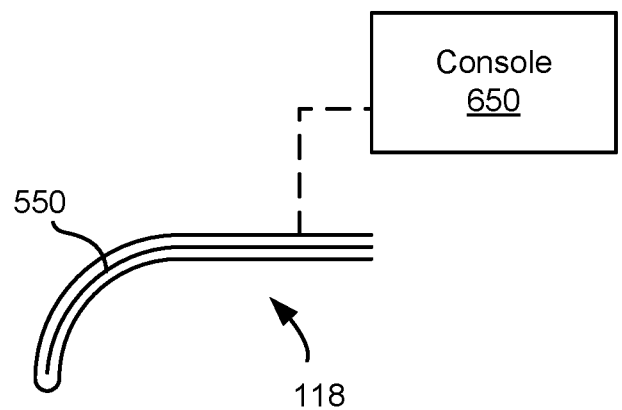
FIG. 6D is a diagram of an endoscope with a shape sensing optical fiber according to one embodiment.

FIG. 6D is a diagram of an endoscope 118 with a shape sensing optical fiber according to one embodiment. The spatial sensor 550 is a shape sensing optical fiber embedded inside the endoscope 118. A console 650 positioned in proximity to the endoscope 118 is coupled to the shape sensing optical fiber. The console 650 transmits light through the shape sensing optical fiber and receives light reflected from the shape sensing optical fiber. The shape sensing optical fiber may include a segment of a fiber Bragg grating (FBG). The FBG reflects certain wavelengths of light, while transmitting other wavelengths. The console 650 generates reflection spectrum data based on the wavelengths of light reflected by the FBG.

The data processing module 160 can analyze the reflection spectrum data to generate position and orientation data of the endoscope 118 in two or three dimensional space. In particular, as the endoscope bends 118, the shape sensing optical fiber embedded inside also bends. The specific wavelengths of light reflected by the FBG changes based on the shape of the shape sensing optical fiber (e.g., a "straight" endoscope is in a different shape than a "curved" endoscope). Thus, the data processing module 160 can determine, for example, how many degrees the endoscope 118 has bent in one or more directions (e.g., in response to commands from the surgical robotic system 100) by identifying differences in the reflection spectrum data. Similar to the EM sensor, the shape sensing optical fiber is suitable for data collection inside the body of the patient because no line-of-sight to the shape sensing optical fiber is required.

V. D. Fluoroscopic Imaging

Figure 6E:
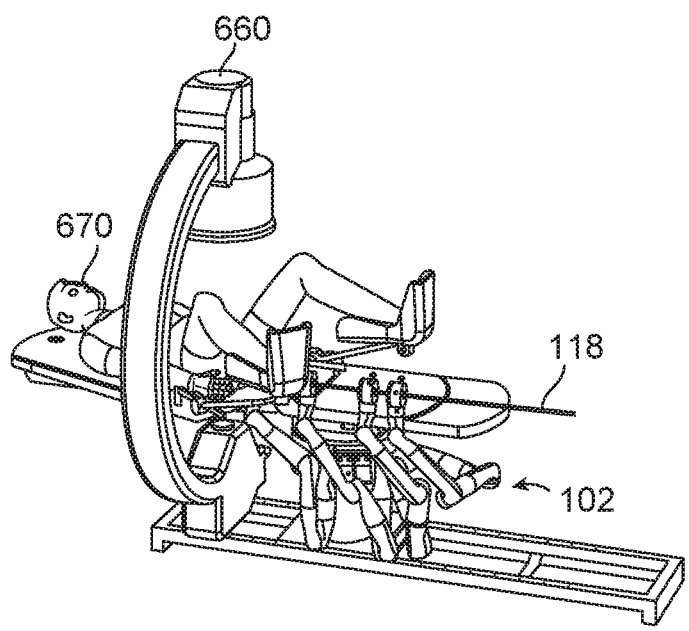
FIG. 6E is a diagram of a fluoroscopic imaging system in proximity to an endoscope according to one embodiment.

FIG. 6E is a diagram of a fluoroscopic imaging system 660 in proximity to an endoscope 118 according to one embodiment. The endoscope 118 is inserted by robotic arms 102 into a patient 670 undergoing a surgical procedure. The fluoroscopic imaging system 660 is a C-arm that includes a generator, detector, and imaging system (not shown). The generator is coupled to the bottom end of the C-arm and faces upward toward the patient 670. The detector is coupled to the top end of the C-arm and faces downward toward the patient 670. The generator emits X-ray waves toward the patient 670. The X-ray waves penetrate the patient 670 and are received by the detector. Based on the received X-ray waves, the fluoroscopic imaging system 660 generates the images of body parts or other objects inside the patient 670 such as the endoscope 118. In contrast to the optical cameras described in Section. V. B. Camera Sensors that capture images of the actual endoscope, the fluoroscopic imaging system 660 generates images that include representations of objects inside the patient 670, e.g., an outline of the shape of an endoscope based on the reflected X-rays. Thus, the data processing module 160 can use similar image processing techniques as previously described such as optical flow to determine the position and motion of the endoscope, e.g., in response to commands from the surgical robotic system 100.

VI. Insertion and Roll Offset

Figure 7A:
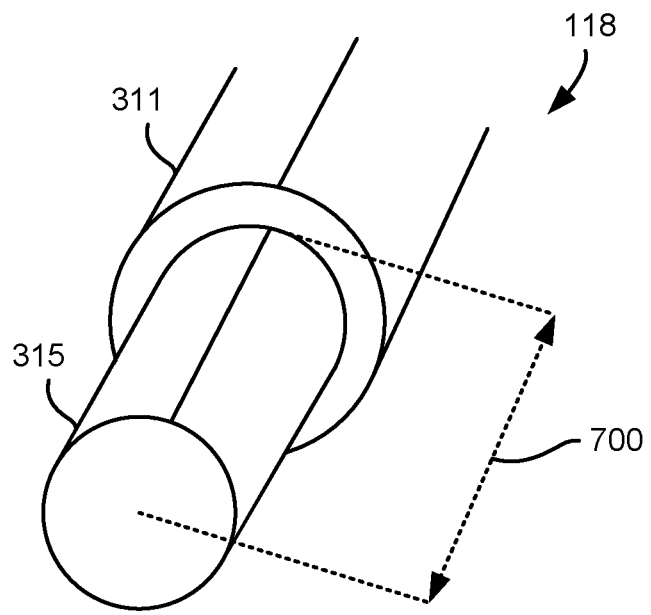
FIG. 7A shows a length of a leader of an endoscope extended outside of a sheath of the endoscope according to one embodiment.

FIG. 7A shows a length 700 of a leader 315 of an endoscope 118 extended outside of a sheath 311 of the endoscope 118 according to one embodiment. As the length 700 increases, the flexibility of the distal end of the leader 315 increases because the length 700 is not as significantly enclosed by the sheath 311. In comparison, the portion of the leader 315 radially enclosed by the sheath 311 is less flexible because the material of the sheath 311 provides more rigidity. In some embodiments, since the physical characteristics of the endoscope varies based on the length of extension, the surgical robotic system 100 needs to provide commands to move the endoscope that account for the extension. For example, the distal end of the endoscope may become heavier (and/or more flexible) as the extension increases because there is more length of the leader outside of the sheath. Thus, to achieve the same bending movement, the surgical robotic system 100 may need to provide a command that translates pull wires of the endoscope to a greater degree relative to a command to move an endoscope with a smaller length of extension.

Figure 7B:
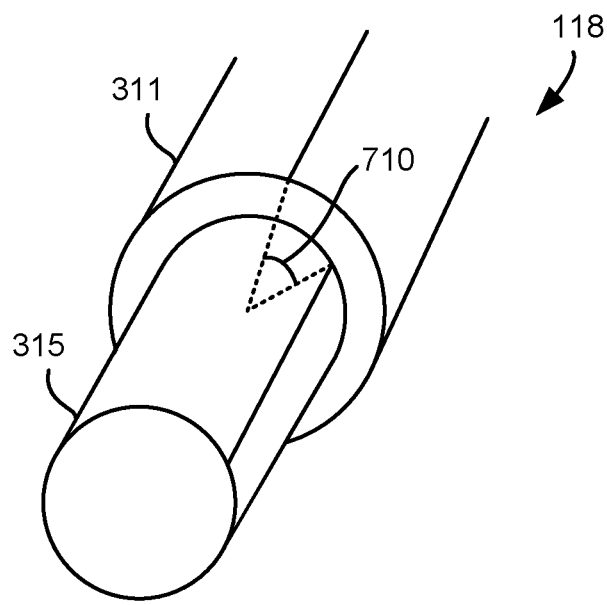
FIG. 7B shows a relative roll angle of the leader of the endoscope relative to the sheath of the endoscope according to one embodiment.

FIG. 7B shows a relative roll angle 710 of the leader 315 of the endoscope 118 relative to the sheath 311 of the endoscope 118 according to one embodiment. The leader 315 and/or the sheath 311 may be more flexible in certain directions compared to other directions, e.g., due to variances in the material of the endoscope 118. Thus, based on the relative roll angle 710, the flexibility of the endoscope 118 may change in a certain direction. In addition to accounting for the length of extension as described above, the surgical robotic system 100 may also need to account for the relative roll angle when providing commands to move the endoscope. For example, a command to bend the endoscope 90 degrees may result in an actual bend of 80 degrees when the relative roll angle is 5 degrees, but may result in an actual bend of 100 degrees when the relative roll angle is −5 degrees.

VII. Calibration

VII. A. Overview

The surgical robotic system 100 performs a calibration process to determine gain values that compensate for imperfections of an endoscope's behavior. During the calibration process, the surgical robotics system 100 moves the endoscope to one or more target positions (or angles) by translating one or more pull wires according to one or more commands. The surgical robotics system 100 receives spatial data indicating actual positions and orientations of the endoscope achieved in response to the commands, where the actual positions may be different than the target positions due to the endoscope's imperfections. The surgical robotics system 100 determines the gain values based on the commands, the target positions desired to be achieved, and the actual positions achieved. The surgical robotics system 100 can perform such a calibration process before a surgical procedure, for example, on a manufacturing line for quality assurance, or in a laboratory or clinical setting. Additionally, the surgical robotics system 100 can perform such a calibration process while performing a surgical procedure on a patient.

As a simple illustrative example, the material of a particular endoscope may be stiffer than expected. When a calibration process is performed, the spatial data indicates that the endoscope deflected to an actual position of 30 degrees in the pitch direction, whereas the target position was 60 degrees. As part of an example calibration process, the surgical robotics system 100 determines that the corresponding gain value for the endoscope is the decimal value of 2.0 because the target position is two times the value of the actual position. In other embodiments, the gain value may be represented using other formats, e.g., a percentage, an integer, in unit of degrees, etc.

Gain values can be associated with a particular pull wire, endoscope, direction of motion (e.g., positive pitch direction, negative yaw direction, or roll direction), and/or other types of factors. In particular, the example described above is a trivial scenario that assumes a constant gain value of 2.0 for all conditions of the endoscope. However, in practice, calibrating endoscopes is a more complex problem because the gain values depend on a plethora of factors, either independently or in combination. For instance, the gain value may be 2.0 in the positive pitch direction, 3.0 in the negative pitch direction, 1.5 in the positive yaw direction, etc. Further, the gain value may be 2.0 in the positive pitch direction for a first pull wire but 2.2 for a second pull wire in the same endoscope. Additionally, the gain value may be 2.0 for the first pull wire of a first endoscope, but 2.5 for the first pull wire of a second endoscope.

In some embodiments, the calibration module 130 receives a length of a leader of the endoscope extended outside of (or radially enclosed by) a sheath of the endoscope and/or a relative roll angle of the leader relative to the sheath. The calibration module 130 determines the gain values further based on the length and/or the relative roll angle. Gain values for a certain length or relative roll angle may differ from gain values for another length or relative roll angle because the endoscope may be more flexible in a particular direction or segment of the endoscope.

In one embodiment, the endoscope (e.g., the leader and/or the sheath) includes multiple segments each having a different level of stiffness. The calibration module 130 receives a Young's modulus of at least one of the segments and determines the gain values further based on the Young's modulus.

In one embodiment, a complete calibration process involves several sub-calibration processes. For example, the surgical robotic system 100 provides a command to move an endoscope to a target position in a first direction. The calibration module 130 receives calibration data indicating an actual position of the endoscope, which may differ from the target position. The surgical robotic system 100 relaxes the endoscope back to a resting position, and repeats the data collection process for a number of other directions. The surgical robotic system 100 can also provide commands to extend the leader to a greater lengths outside of the sheath, and repeat the calibration data collection process for a number of different lengths of extension. Similarly, the surgical robotic system 100 can provide commands to rotate the leader to a relative roll angle relative to the sheath, and repeat the calibration data collection process for a number of different relative roll angles.

The calibration module 130 determines gain values based on an aggregate calibration dataset from each of the sub-calibration processes. As evident by the number of potential combination of factors to consider during calibration, the calibration process may become a more complex process with many nested loops of different tests. Thus, it is advantageous to automate the calibration using the surgical robotic system 100, e.g., to help keep track of all the factors that need to be tested, reduce the chance for calibration errors or oversights, and eliminate the need for a user to manually conduct rote tasks for each test.

In some embodiments, the calibration module 130 stores the calibration data and associated gain values with one or more other factors (e.g., information about the corresponding command to move the endoscope, a direction of movement, an identifier of a certain pull wire, a length and/or relative roll angle of the leader relative to the sheath, or a unique identifier of the endoscope) in the calibration store 140. The calibration module 130 may upload the calibration data, gain values, and/or factors to a global calibration database including information from multiple endoscopes.

VII. B. Calibration Models

The surgical robotic system 100 may use one or more types of models to generate commands to move an endoscope appropriately based on the calibration data. In particular, the command module 150 generates a command for each pull wire of an endoscope based on parameters of one of the models, where the parameters and associated gain values are determined based on the calibration data. The parameters may be the same as the gain values for some models, while for other models, the surgical robotic system 100 may determine the gain values based on the parameters. The models may be associated with the leader, sheath, or both the leader and sheath of an endoscope. Embodiments of models that are associated with both the leader and sheath account for parameters describing interaction between the leader and sheath, e.g., the length of extension and relative roll angle of the leader relative to the sheath.

In one embodiment, the calibration module 130 uses an empirical model implemented with a matrix of gain values. The gain values are empirically determined by solving a set of linear equations based on calibration data from previously completed calibration processes. The calibration module 130 can multiply a vector representing the input command (e.g., including a target translation for each pull wire of an endoscope as well as extension and relative roll values) by the matrix of gain values can generate an output vector representing an adjusted command (e.g., including modified translations for one or more of the pull wires). The empirical model gain values may compensate for pull-wire specific compression or expansion based on bending of the endoscope. In particular, the distance that a certain pull wire travels inside the endoscope may shrink or lengthen based on the curvature of the endoscope. In some embodiments, the empirical model accounts for the dependency between wires in opposing directions. For example, a first wire corresponds to the positive pitch direction and a second wire corresponds to the negative pitch direction. Providing slack on the first wire while pulling on the second wire both contribute to the same motion of bending the endoscope in the negative pitch direction.

In one embodiment, the calibration module 130 uses a physics based model to determine the effective physical properties of the endoscope as it bends. The physics based model has the potential to more fully capture the behavior of the endoscope. As a comparison, a trivial model may assume that a bent endoscope bends uniformly throughout a particular length of the endoscope according to a given bending stiffness in that particular length and remains straight throughout the rest of the length of the endoscope. Further, the physics based model may decompose the leader and sheath of the endoscope into individual segments that each have an associated bending stiffness. The physics based model also considers the stiffness of the pull wires and the effect of the sheath and leader interaction (e.g., extension length and relative roll angle) on the stiffness of any particular segment.

With the physics based model, the computer system 120 may use inverse solid mechanics to translate commands to move the endoscope (e.g., indicating an angle to bend in pitch and/or yaw directions) into distances that the surgical robotic system 100 should translate one or more pull wires to achieve the desired motion. Further, by using the physics based model, the robotic system 100 may move one or more IDMs to compensate for any unwanted motion of the endoscope's distal tip as a result of axial deformations coupled to bending motions.

In one embodiment, the calibration module 130 uses a model-less inversion process to generate commands to move the endoscope. For example, the calibration module 130 implements a lookup table that does not require the use of gain values and/or parameters. Instead, the lookup table maps previously recorded input values (e.g., commands to move the endoscope in pitch and yaw directions) to output values (e.g., translation for each pull wire of the endoscope) based on calibration data. The lookup table may interpolate (e.g., solved via Delaunay triangulation or other multidimensional triangulations techniques) or extrapolate between data points if the exact input-to-output mapping is not known, e.g., bending 42 degrees can be interpolated using data points for 40 degrees and 45 degrees. To reduce the amount of computational resources required for the computer system 120 to execute the lookup table, the calibration module 130 can minimize the size of the data set of mappings by using techniques such as Taylor decomposition or approximating the data set using a Fourier representation.

VII. C. Example Process Flows

Figure 8A:
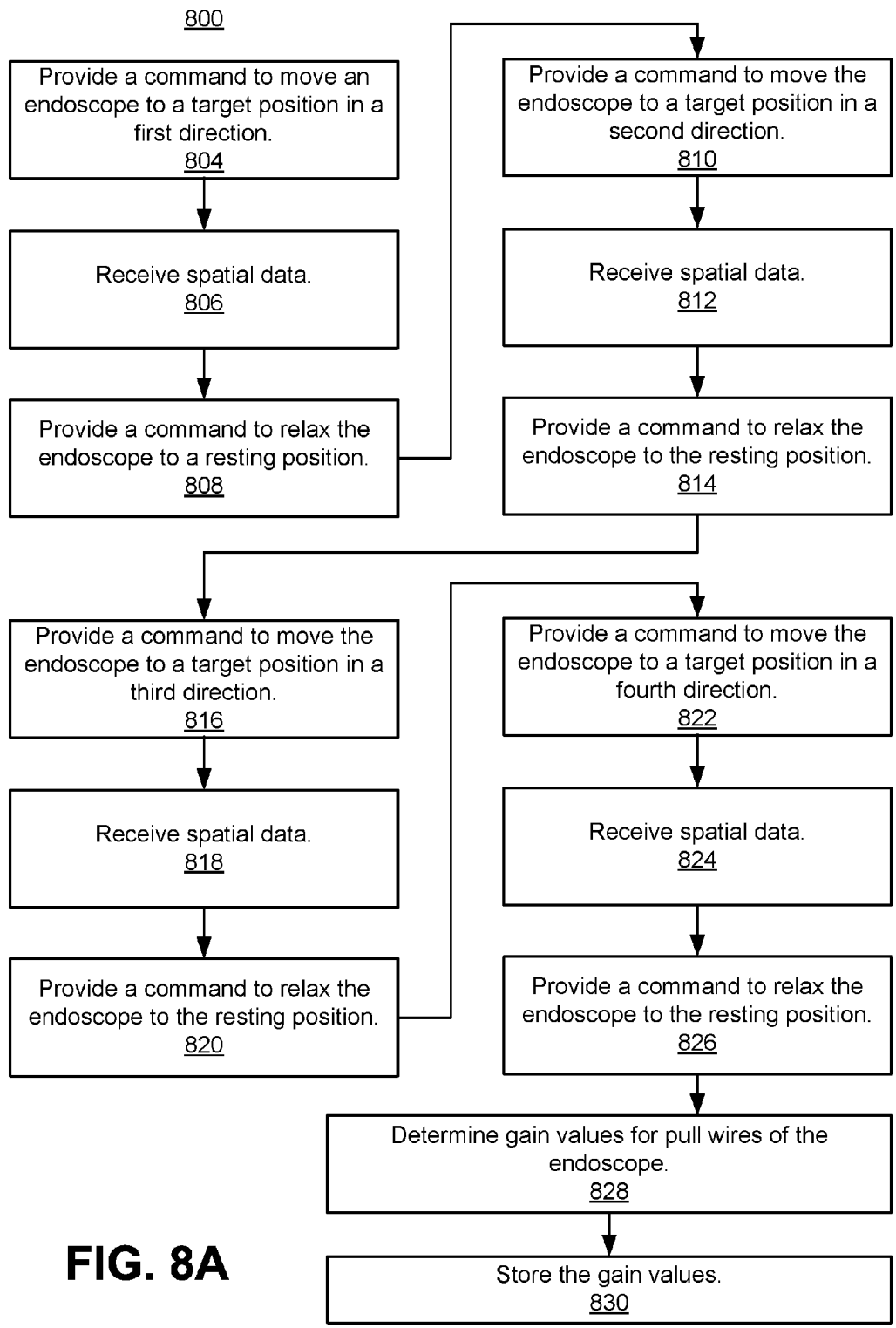
FIG. 8A is a flowchart of a process for automated calibration of an endoscope according to one embodiment.

FIG. 8A is a flowchart of a process 800 for automated calibration of an endoscope according to one embodiment. The process 800 may include different or additional steps than those described in conjunction with FIG. 8A in some embodiments, or perform steps in different orders than the order described in conjunction with FIG. 8A. The process 800 is particular for calibrating an embodiment of an endoscope including four pull wires, e.g., each separated by 90 degrees and corresponding to the, positive or negative, pitch or yaw directions. However, the process 800 can be generalized to any number of pull wires, and further discussed with reference to FIG. 8B. Since the computer system 120 is capable of automating the process 800, a user does not have to manually perform a calibration procedure to use the surgical robotic system 100. Automated calibration is advantageous, e.g., because the process reduces the time required to calibrate an endoscope.

The command module 150 provides 804 a command to move an endoscope to a target position in a first direction. The calibration module 130 receives 806 spatial data indicating an actual position and orientation of the endoscope, which moved in response to the command. The spatial data can be received from spatial sensors (e.g., coupled to the endoscope or positioned in proximity to the endoscope) such as accelerometers, gyroscopes, fiducial markers, fiber optic cables, cameras, or an imaging system, as previously described in Section V. Spatial Sensors. The spatial data describes the position and/or orientation of the endoscope—or a portion of the endoscope—in one or more directions of movement. The command module 150 provides 808 a command to relax the endoscope to a resting position.

The command module 150 provides 810 a command to move the endoscope to the target position in a second direction. The calibration module 130 receives 812 spatial data. The command module 150 provides 814 a command to relax the endoscope to the resting position.

The command module 150 provides 816 a command to move the endoscope to the target position in a third direction. The calibration module 130 receives 818 spatial data. The command module 150 provides 820 a command to relax the endoscope to the resting position.

The command module 150 provides 822 a command to move the endoscope to the target position in a fourth direction. The calibration module 130 receives 824 spatial data. The command module 150 provides 826 a command to relax the endoscope to the resting position.

The target position may remain constant for each of the four directions. In some embodiments, the target position varies between different directions. For instance, the target position is 90 degrees for the first and third directions and 45 degrees for the second and fourth directions. The first, second, third, and fourth directions may be the positive pitch, positive yaw, negative pitch, and negative yaw directions, in any particular order. In other embodiments, the commands move the endoscope toward the target position simultaneously in two or more directions, e.g., 60 degrees in both the positive pitch and positive yaw directions. Though process 800 involves four directions, in other embodiments, the computer system 120 can repeat the steps 804 through 808 for any other number of directions (more or fewer).

The calibration module 130 determines 828 gain values for pull wires of the endoscope based on the spatial data for one or more of the directions. The calibration module 130 may determine a gain value associated with each pull wire. At least one of the gain values may have a value different from unity. A unity gain value indicates that the corresponding pull wire exhibits ideal behavior, e.g., the actual motion of the endoscope matches the target motion based on translation of the corresponding pull wire. In some embodiments, the calibration module 130 retrieves default gain values (e.g., determined in a previous calibration process) for the pull wires and determines the gain values further based on the default gain values.

The calibration module 130 stores 830 the gain values in the calibration store 140. The endoscope may include a computer readable tangible medium, e.g., flash memory or a database, to store the gain values. In some embodiments, the command module 150 provides a command to modify the length and/or relative roll angle of the leader relative to the sheath, and the surgical robotic system 100 repeats steps of the process 800 to determine gain values associated with the modified length and/or relative roll angle.

Figure 8B:
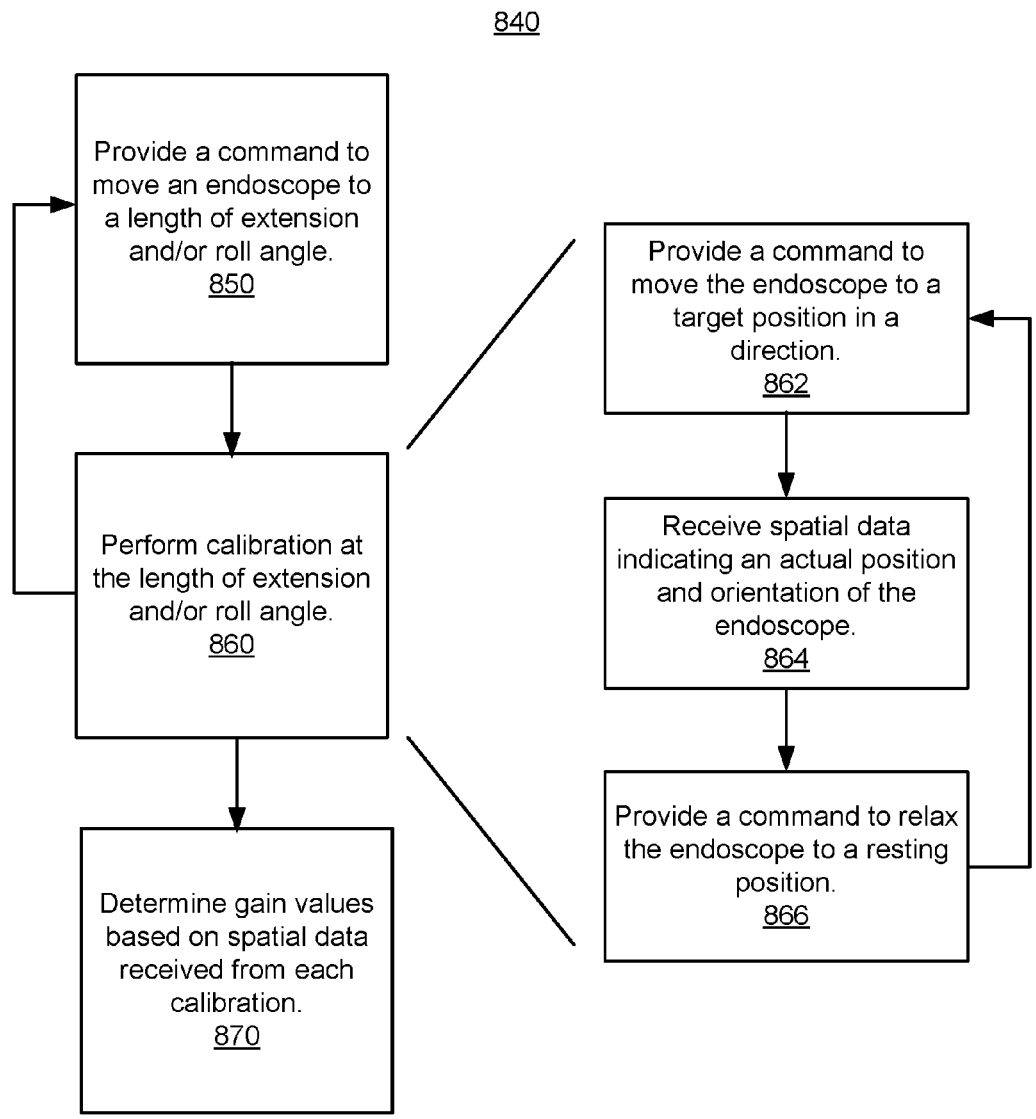
FIG. 8B is a flowchart of a process for automated calibration of an endoscope based on length of extension and relative roll angle according to one embodiment.

FIG. 8B is a flowchart of a process 840 for automated calibration of an endoscope based on length of extension and relative roll angle according to one embodiment. The process 840 may include different or additional steps than those described in conjunction with FIG. 8B in some embodiments, or perform steps in different orders than the order described in conjunction with FIG. 8B. In contrast to the process 800, the process 840 is generalized to any number of directions, as well as any number of lengths of extension and relative roll angles of the leader relative to the sheath of an endoscope. For instance, instead of an endoscope with four pull wires offset from each other by 90 degrees, an endoscope may include three pull wires offset from each other by 120 degrees, or in any other configuration with different offset angles (e.g., at the 11 o'clock, 2 o'clock, and 6 o'clock hand positions of a clock).

The surgical robotic system 100 provides 850 a command to move an endoscope to a length or extension and/or relative roll angle. The surgical robotic system 100 performs 860 calibration at the length or extension and/or relative roll angle. In step 860, the command module 150 provides 862 a command to move the endoscope to a target position in a direction. The calibration module 130 receives 864 spatial data indicating an actual position and orientation of the endoscope. The command module 150 provides 866 a command to relax the endoscope to a resting position. The surgical robotic system 100 repeats the steps 862-866 for each direction in a set of directions. Further, the surgical robotic system 100 repeats the steps 850-860 for each length of extension and/or relative roll angle (or combination of lengths of extension and relative roll angles) in a set of different lengths of extension and/or relative roll angles. The calibration module 130 determines 870 gain values based on spatial data received from each calibration.

FIG. 9 is a flowchart of a process 900 for intraoperative automated calibration of an endoscope to one embodiment. The process 900 may include different or additional steps than those described in conjunction with FIG. 9 in some embodiments, or perform steps in different orders than the order described in conjunction with FIG. 9. In some embodiments, the command console 200 may use the process 900 in the velocity mode or position control mode previously described in Section II. Command Console.

The calibration module 130 retrieves 910 default gain values for an endoscope including pull wires, a leader, and a sheath. Each pull wire may be associated with one of the default gain values. The surgical robotic system 100 inserts 920 the endoscope into a patient undergoing a surgical procedure, e.g., ureteroscopy, percutaneous nephrolithotomy (PCNL), colonoscopy, fluoroscopy, prostatectomy, colectomy, cholecystectomy, inguinal hernia, and bronchoscopy. The calibration module 130 receives 930 information about a relative roll angle of the leader relative to the sheath and a length of the leader radially enclosed by the sheath. The information about the relative roll angle and the length may be based on previous commands provided to move the endoscope, a default relative roll angle and length value, or data generated by sensors (e.g., an accelerometer and gyroscope coupled to the endoscope). The command module 150 provides 940 a command to move the endoscope by translating at least one of the pull wires.

The calibration module 130 receives 950 spatial data of the endoscope having been moved in response to the command. In one embodiment, the spatial data is received from a fluoroscopic imaging system. The fluoroscopic imaging system can capture images of the endoscope inside the patient, which enables the surgical robotic system 100 to perform the process 900 during a surgical procedure. The calibration module 130 determines 960 a new gain value based on the spatial data, the corresponding default gain value, the length of extension, the relative roll angle, and/or the command. The calibration module 130 stores 970 the new gain value in the calibration store 140. The surgical robotic system 100 can generate additional commands based on new gain values determined by the process 900. For example, the endoscope moves to an actual position of 80 degrees in response to a first command, where the target position is actually 90 degrees. The command module 150 generates a new command based on the new gain values and provides the new command to move the endoscope using the surgical robotic system 100. Since the new command compensates for the angle discrepancy (that is, 80 degrees is 10 degrees short of 90 degrees), the endoscope moves to an actual position of 90 degrees in response to the new command.

VIII. Alternative Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

What is claimed is:

1. A method comprising:
   retrieving, from computer readable media storing calibration data, a plurality of default gain values each associated with a pull wire of a plurality of pull wires of an endoscope;
   inserting the endoscope into a body of a patient using a surgical robotic system;
   providing a command, derived at least partly from one or more of the plurality of default gain values, to move the endoscope by translating at least one of the plurality of pull wires using the surgical robotic system;
   receiving spatial data indicating an actual position of the endoscope having been moved in response to the command;
   determining, for at least one of the pull wires, a new gain value based on the spatial data; and
   storing the new gain value in the computer readable media.

2. The method of claim 1, further comprising:
   generating a second command based on the new gain value; and
   providing the second command to move the endoscope using the surgical robotic system.

3. The method of claim 1, wherein receiving the spatial data comprises:
   positioning a fluoroscopic imaging system in proximity to the endoscope; and
   capturing a plurality of fluoroscopic images of the endoscope by the fluoroscopic imaging system.

4. The method of claim 1, wherein the surgical robotic system deflects the endoscope to an angle in a yaw direction and a pitch direction in response to the command.

5. The method of claim 1, wherein the endoscope comprises at least one electromagnetic (EM) sensor coupled to a distal end of the endoscope, and wherein the method further comprises:
   positioning at least one EM field generator in proximity to the EM sensor; and
   wherein receiving the spatial data comprises detecting, at the EM sensor, an EM field whose strength is a function of the actual position of the distal end of the endoscope containing the EM sensor.

6. The method of claim 1, wherein the endoscope comprises one or more spatial sensors coupled to a distal end of the endoscope, the one or more spatial sensors including at least one of an accelerometer or a gyroscope, and wherein receiving the spatial data comprises detecting, by the one or more spatial sensors, motion in at least one direction.

7. The method of claim 1, wherein the endoscope comprises an optical fiber embedded inside the endoscope, wherein the method further comprises:
   positioning a console in proximity to the endoscope, the console coupled to the optical fiber and configured to generate reflection spectrum data based on light reflected by the optical fiber; and
   wherein receiving the spatial data comprises analyzing the reflection spectrum data.

8. The method of claim 1, wherein the endoscope includes a camera lens and a working channel, and wherein the camera lens and the working channel are each non-concentric to each pull wire of the plurality of pull wires.

9. The method of claim 1, wherein the endoscope includes a sheath tubular component and a leader tubular component, the sheath tubular component including a first pull wire of the plurality of pull wires, and the leader tubular component including a second pull wire of the plurality of pull wires.

10. The method of claim 9, wherein the leader tubular component and the sheath tubular component each include a plurality of segments.

11. The method of claim 10, wherein the first pull wire of the plurality of pull wires is spiraled at a first angle along a first segment of the plurality of segments of the sheath tubular component.

12. The method of claim 11, wherein the second pull wire of the plurality of pull wires is spiraled at a second angle along a second segment of the plurality of segments of the leader tubular component.

13. The method of claim 9, further comprising:
receiving information indicating a roll angle of the leader tubular component relative to the sheath tubular component and a length of the leader tubular component radially enclosed by the sheath tubular component; and
wherein the new gain value is further determined based on at least one of the roll angle and the length.

14. The method of claim 1, wherein moving the endoscope by translating the at least one of the plurality of pull wires using the surgical robotic system comprises:
providing the command to a plurality of robotic arms coupled to the endoscope.

15. The method of claim 1, wherein the at least one of the plurality of pull wires includes a first pull wire and a second pull wire, and wherein providing the command comprises:
providing a first subcommand to translate the first pull wire a first distance; and
providing a second subcommand to translate the second pull wire a second distance.

16. The method of claim 1, wherein the plurality of default gain values are determined during a calibration process.

17. The method of claim 16, wherein the plurality of default gain values are based at least on a discrepancy between a target position and an actual position of the endoscope.

18. A surgical robotic system comprising:
one or more robotic arms;
an endoscope comprising a plurality of pull wires;
non-transitory computer-readable storage media storing instructions that when executed by a processor cause the processor to perform steps including:
retrieve a plurality of default gain values each associated with one of the pull wires;
insert the endoscope into a body of a patient using the one or more robotic arms;
provide a command, derived from one or more of the plurality of default gain values, to move the endoscope by translating at least one of the plurality of pull wires using the one or more robotic arms;
receive spatial data indicating an actual position of the endoscope having been moved in response to the command;
determining, for at least one of the pull wires, a new gain value based on the spatial data; and
storing the new gain value.

19. The surgical robotic system of claim 18, wherein the steps further include:
generating a second command based on the new gain value; and
providing the second command to move the endoscope using the one or more robotic arms.

20. The surgical robotic system of claim 18, wherein receiving the spatial data comprises:
retrieving a plurality of fluoroscopic images of the endoscope captured by a fluoroscopic imaging system.

21. The surgical robotic system of claim 18, wherein the one or more robotic arms deflects the endoscope to an angle in a yaw direction and a pitch direction in response to the command.

22. The surgical robotic system of claim 18, wherein the endoscope comprises at least one electromagnetic (EM) sensor coupled to a distal end of the endoscope, and wherein receiving the spatial data comprises:
detecting, at the EM sensor, an EM field whose strength is a function of the actual position of the distal end of the endoscope containing the EM sensor relative to an EM field generator.

23. The surgical robotic system of claim 18, wherein the endoscope comprises one or more spatial sensors coupled to a distal end of the endoscope, the one or more spatial sensors including at least one of an accelerometer or a gyroscope, and wherein receiving the spatial data comprises detecting, by the one or more spatial sensors, motion in at least one direction.

24. The surgical robotic system of claim 18, wherein the endoscope comprises an optical fiber embedded inside the endoscope, and wherein receiving the spatial data comprises:
analyzing reflection spectrum data generated based on light reflected by the optical fiber.

25. The surgical robotic system of claim 18, wherein the endoscope includes a camera lens and a working channel, and wherein the camera lens and the working channel are each nonconcentric to each pull wire of the plurality of pull wires.

26. The surgical robotic system of claim 18, wherein the endoscope comprises a sheath tubular component and a leader tubular component, the sheath tubular component including a first pull wire of the plurality of pull wires, and the leader tubular component including a second pull wire of the plurality of pull wires.

27. The surgical robotic system of claim 26, wherein the leader tubular component and the sheath tubular component each include a plurality of segments.

28. The surgical robotic system of claim 27, wherein the first pull wire of the plurality of pull wires is spiraled at a first angle along a first segment of the plurality of segments of the sheath tubular component.

29. The surgical robotic system of claim 28, wherein the second pull wire of the plurality of pull wires is spiraled at a second angle along a second segment of the plurality of segments of the leader tubular component.

30. The surgical robotic system of claim 26, further comprising:
receiving information indicating a roll angle of the leader tubular component relative to the sheath tubular component and a length of the leader tubular component radially enclosed by the sheath tubular component; and
wherein the new gain value is further determined based on at least one of the roll angle and the length.

31. The surgical robotic system of claim 18, wherein the one or more robotic arms includes at least a first robotic arm and a second robotic arm, and wherein moving the endoscope by translating the at least one of the plurality of pull wires using the one or more robotic arms comprises:

providing a first subcommand to the first robotic arm; and
providing a second subcommand, being different than the first subcommand, to the second robotic arm.

32. The surgical robotic system of claim 18, wherein the at least one of the plurality of pull wires includes a first pull wire and a second pull wire, and wherein providing the command comprises:
providing a first subcommand to translate the first pull wire a first distance; and
providing a second subcommand to translate the second pull wire a second distance.

\* \* \* \* \*